(12) United States Patent
van Eijk et al.

(10) Patent No.: US 8,071,310 B2
(45) Date of Patent: Dec. 6, 2011

(54) METHOD FOR THE HIGH THROUGHPUT SCREENING OF TRANSPOSON TAGGING POPULATIONS AND MASSIVE PARALLEL SEQUENCE IDENTIFICATION OF INSERTION SITES

(75) Inventors: Michael Josephus Theresia van Eijk, Herpen (NL); Antonius Gerardus Marie Gerats, Ooij (NL); Adrianus Johannes van Tunen, Wageningen (NL); Michiel Marcel Albert Vandenbussche, Nijmegen (NL)

(73) Assignee: Keygene NV, Wageningen (NL)

( * ) Notice: Subject to any disclaimer, the term of this patent is extended or adjusted under 35 U.S.C. 154(b) by 506 days.

(21) Appl. No.: 12/093,574

(22) PCT Filed: Nov. 8, 2006

(86) PCT No.: PCT/NL2006/000561
§ 371 (c)(1),
(2), (4) Date: Aug. 29, 2008

(87) PCT Pub. No.: WO2007/055568
PCT Pub. Date: May 18, 2007

(65) Prior Publication Data
US 2009/0208943 A1      Aug. 20, 2009

Related U.S. Application Data

(63) Continuation of application No. PCT/NL06/00561, filed on Nov. 8, 2006.

(60) Provisional application No. 60/735,878, filed on Nov. 14, 2005, provisional application No. 60/850,274, filed on Oct. 10, 2006.

(51) Int. Cl.
*C12Q 1/68* (2006.01)

(52) U.S. Cl. ................................ 435/6.12; 435/91.2
(58) Field of Classification Search .................. None
See application file for complete search history.

(56) References Cited

U.S. PATENT DOCUMENTS

2004/0014957 A1 * 1/2004 Eldrup et al. ............... 536/23.1
(Continued)

FOREIGN PATENT DOCUMENTS

WO      0023620      4/2000
(Continued)

OTHER PUBLICATIONS

C. Sallaud, et al., "Highly efficient production and characterization of T-DNA plants for rice (*Oryza sativa* L.) functional genomics", Theor. Appl. Genet., vol. 106, No. 8, May 2003, pp. 1396-1408.
Michiel Vandenbussche, et al., "Toward the Analysis of the *Petunia* MADS Box Gene Family by Reverse and Forward Transposon Insertion Mutagenesis Approaches: B, C, and D Floral Organ Identity Functions Require Sepallata-Like MADS Box Genes in *Petunia*", The Plant Cell, vol. 15, No. 11, Nov. 2003, pp. 2680-2693.

(Continued)

*Primary Examiner* — Samuel Woolwine
(74) *Attorney, Agent, or Firm* — Browdy and Neimark, PLLC

(57) ABSTRACT

A method for the identification of a gene in a transposon population is provided. The method comprises isolating genomic DNA, optionally pooling the DNA, restricting the DNA in the pools using an enzyme, ligating adaptors, amplifying the adaptor-ligated fragments with primers one of which is a primer complementary to a border of a transposon sequence, sequencing the fragments using high throughput sequencing, aligning the fragments with known sequences in a database and thereby identifying gene candidates.

15 Claims, 10 Drawing Sheets

U.S. PATENT DOCUMENTS

2004/0058349 A1* 3/2004 Van Ness et al. .................. 435/6
2005/0059057 A1* 3/2005 Maes et al. ......................... 435/6
2005/0130173 A1* 6/2005 Leamon et al. .................... 435/6

FOREIGN PATENT DOCUMENTS

WO 2004069849 A2 8/2004
WO 2004070005 A2 8/2004

OTHER PUBLICATIONS

Vadim V. Demidov, et al., "PNA and LNA throw light on DNA", Trends in Biotechnology, vol. 21, No. 1, Jan. 2003, pp. 4-7.

* cited by examiner

| SEQ ID NO. | | |
|---|---|---|
| SEQ ID No. 28 | Arabidopsis_AGL62 | MVKKSKGRQKIEMVKMKNESNLQVTFSKRRSGLFKKASELCTLCGAEVAIVVFSP-GRKVFSFGHPNVDSVIDRFIN |
| SEQ ID No. 29 | tag09_00297446 | CTLCGAEVAILAFAPNSNKVYSFGHPC |
| SEQ ID No. 30 | tag17_00017391 | CTLCGAEVAILAFAPNSNKVYSFGHPC |
| SEQ ID No. 31 | tag29_00035549 | CTLCGAEVAILAFAPNSNKVYSFGHPC |
| SEQ ID No. 32 | tag29_00050666 | CTLCGAEVAILAFAPNSNKVYSFGHPC |

Insert position

Fig. 4

| SEQ ID No. | Tag | Sequence |
|---|---|---|
| SEQ ID No. 33 | tag06_000179 | TAAACTGGTAGCTCCGCCCCTGGAGATGGTGCATGCAAAGCAGCGTATGATAAAAAGGAGTTCATGTTGAAGCAAATCAAGA |
| SEQ ID No. 34 | tag06_000915 | TAAACTGGTAGCTCCGCCCCTGGAGATGGTGCATGCAAAGCAGCGTATGATAAAAAGGAGTTCATGTTGAAGCAAATCAAGA |
| SEQ ID No. 35 | tag20_002065 | TAACATGGTAGCTCCGCCCCTGGAGATGGTGCATGCAAAGCAGCGTATGATAAAAAGGAGTTCATGTTGAAGCAAATCAAGA |
| SEQ ID No. 36 | tag29_000529 | TAAGACAGTAGCTCCGCCCCTGGAGATGGTGCATGCAAAGCAGCGTATGATAAAAAGGAGTTCATGTTGAAGCAAATCAAGA |
| SEQ ID No. 37 | tag20_001114 | TAACATGGTAGCTCCGCCCCCTGACTTTTGTTTGCACTAAGAAAATTGCTTACTCAGGACTCATCGTCCAATT |
| SEQ ID No. 38 | tag20_001985 | TAACATGGTAGCTCCGCCCCCTGACTTTTGTTTGCACTAAGAAAATTGCTTACTCAGGACTCATCGTCCAATT |
| SEQ ID No. 39 | tag28_000270 | TAACTGTGTAGCTCCGCCCCTGACTTTTGTTTGCACTAAGAAAATTGCTTACTCAGGACTCATCGTCCAATT |
| SEQ ID No. 40 | tag10_002046 | TAAAGCTGTAGCTCCGCCCCTGGCAAACAATGAGATAAACAATAATAAATAAATAAATGAAATCAGTAAAGCTTATTGTATTTGAA |
| SEQ ID No. 41 | tag10_002567 | TAAAGCTGTAGCTCCGCCCCTGGCAAACAATGAGATAAACAATAATAAATAAATAAATGAAATCAGTAAAGCTTATTGTATTTGAA |
| SEQ ID No. 42 | tag10_002741 | TAAAGCTGTAGCTCCGCCCCTGGCAAACAATGAGATAAACAATAATAAATAAATAAATGAAATCAGTAAAGCTTATTGTATTTGAA |
| SEQ ID No. 43 | tag13_000028 | TAAATCGGTAGCTCCGCCCCTGGCAAACAATGAGATAAACAATAATAAATAAATAAATGAAATCAGTAAAGCTTATTGTATTTGAA |
| SEQ ID No. 44 | tag13_001415 | TAAATCGGTAGCTCCGCCCCTGGCAAACAATGAGATAAACAATAATAAATAAATAAATGAAATCAGTAAAGCTTATTGTATTTGAA |
| SEQ ID No. 45 | tag13_001898 | TAAATCGGTAGCTCCGCCCCTGGCAAACAATGAGATAAACAATAATAAATAAATAAATGAAATCAGTAAAGCTTATTGTATTTGAA |
| SEQ ID No. 46 | tag28_000833 | TAACTGTGTAGCTCCGCCCCTGGCAAACAATAAAACAATAATAAATAAATAAATGAAATCAGTAAAGCTTATTGTATTTGAA |
| SEQ ID No. 47 | tag28_000844 | TAACTGTGTAGCTCCGCCCCTGGCAAACAATAAAACAATAATAAATAAATAAATGAAATCAGTAAAGCTTATTGTATTTGAA |

SEQUENCE LISTING

```
<160> NUMBER OF SEQ ID NOS: 47

<210> SEQ ID NO 1
<211> LENGTH: 17
<212> TYPE: DNA
<213> ORGANISM: artificial
<220> FEATURE:
<223> OTHER INFORMATION: adapter or primer
```

<400> SEQUENCE: 1
ctcgtagact gcgtacg                                                      17

<210> SEQ ID NO 2
<211> LENGTH: 15
<212> TYPE: DNA
<213> ORGANISM: artificial
<220> FEATURE:
<223> OTHER INFORMATION: adapter or primer

<400> SEQUENCE: 2
ctgacgcatg cttaa                                                        15

<210> SEQ ID NO 3
<211> LENGTH: 16
<212> TYPE: DNA
<213> ORGANISM: artificial
<220> FEATURE:
<223> OTHER INFORMATION: adapter or primer

<400> SEQUENCE: 3
gacgatgagt cctgag                                                       16

<210> SEQ ID NO 4
<211> LENGTH: 14
<212> TYPE: DNA
<213> ORGANISM: artificial
<220> FEATURE:
<223> OTHER INFORMATION: adapter or primer

<400> SEQUENCE: 4
tactcaggac tcat                                                         14

<210> SEQ ID NO 5
<211> LENGTH: 21
<212> TYPE: DNA
<213> ORGANISM: artificial
<220> FEATURE:
<223> OTHER INFORMATION: adapter or primer

<400> SEQUENCE: 5
agactgtgta cgaattgaca c                                                 21

<210> SEQ ID NO 6
<211> LENGTH: 19
<212> TYPE: DNA
<213> ORGANISM: artificial
<220> FEATURE:
<223> OTHER INFORMATION: adapter or primer

<400> SEQUENCE: 6
gacgatgagt cctgagtaa                                                    19

<210> SEQ ID NO 7
<211> LENGTH: 29
<212> TYPE: DNA
<213> ORGANISM: artificial
<220> FEATURE:
<223> OTHER INFORMATION: adapter or primer
<220> FEATURE:
<221> NAME/KEY: misc_feature
<222> LOCATION: (11)..(14)
<223> OTHER INFORMATION: N= A, C, T or G

<400> SEQUENCE: 7
catatattaa nnnngtagct ccgcccctg                                         29

```
<210> SEQ ID NO 8
<211> LENGTH: 19
<212> TYPE: DNA
<213> ORGANISM: artificial
<220> FEATURE:
<223> OTHER INFORMATION: adapter or primer

<400> SEQUENCE: 8
gacgatgagt cctgagtaa                                              19

<210> SEQ ID NO 9
<211> LENGTH: 31
<212> TYPE: DNA
<213> ORGANISM: artificial
<220> FEATURE:
<223> OTHER INFORMATION: adapter or primer

<400> SEQUENCE: 9
catatacaat tggacgatga gtcctgagta a                                31

<210> SEQ ID NO 10
<211> LENGTH: 44
<212> TYPE: DNA
<213> ORGANISM: artificial
<220> FEATURE:
<223> OTHER INFORMATION: adapter or primer

<400> SEQUENCE: 10
cctatcccct gtgtgccttg cctatcccct gttgcgtgtc tcag                  44

<210> SEQ ID NO 11
<211> LENGTH: 44
<212> TYPE: DNA
<213> ORGANISM: artificial
<220> FEATURE:
<223> OTHER INFORMATION: adapter or primer

<400> SEQUENCE: 11
aggggacaca cggaacggat aggggacaac gcacagagtc ttaa                  44

<210> SEQ ID NO 12
<211> LENGTH: 44
<212> TYPE: DNA
<213> ORGANISM: artificial
<220> FEATURE:
<223> OTHER INFORMATION: adapter or primer

<400> SEQUENCE: 12
ccatctcatc cctgcgtgtc ccatctgttc cctccctgtc tcag                  44

<210> SEQ ID NO 13
<211> LENGTH: 42
<212> TYPE: DNA
<213> ORGANISM: artificial
<220> FEATURE:
<223> OTHER INFORMATION: adapter or primer

<400> SEQUENCE: 13
gagtagggac gcacagggta gacaagggag ggacagagtc at                    42

<210> SEQ ID NO 14
<211> LENGTH: 20
<212> TYPE: DNA
<213> ORGANISM: artificial
<220> FEATURE:
<223> OTHER INFORMATION: adapter or primer
```

<400> SEQUENCE: 14
cctatcccct gtgtgcctttg                                              20

<210> SEQ ID NO 15
<211> LENGTH: 20
<212> TYPE: DNA
<213> ORGANISM: artificial
<220> FEATURE:
<223> OTHER INFORMATION: adapter or primer

<400> SEQUENCE: 15
ccatctcatc cctgcgtgtc                                               20

<210> SEQ ID NO 16
<211> LENGTH: 99
<212> TYPE: DNA
<213> ORGANISM: Artificial Sequence
<220> FEATURE:
<223> OTHER INFORMATION: sequence of adapter ligated with DNA fragment

<400> SEQUENCE: 16
taaagacgta gctccgcccc tgaccattat attttattga agtattattg ttgatcattg    60
atatccatta tattcatttg ctttagatta tcatatctt                          99

<210> SEQ ID NO 17
<211> LENGTH: 99
<212> TYPE: DNA
<213> ORGANISM: Artificial Sequence
<220> FEATURE:
<223> OTHER INFORMATION: sequence of adapter ligated with DNA fragment

<400> SEQUENCE: 17
taaagacgta gctccgcccc tgaccattat attttattga agtattattg ttgatcattg    60
atatccatta tattcatttg ctttagatta tcatatctt                          99

<210> SEQ ID NO 18
<211> LENGTH: 99
<212> TYPE: DNA
<213> ORGANISM: Artificial Sequence
<220> FEATURE:
<223> OTHER INFORMATION: sequence of adapter ligated with DNA fragment

<400> SEQUENCE: 18
taaagacgta gctccgcccc tgaccattat attttattga agtattattg ttgatcattg    60
acatccatta tattcatttg ctttagatta tcatatctt                          99

<210> SEQ ID NO 19
<211> LENGTH: 99
<212> TYPE: DNA
<213> ORGANISM: artificial
<220> FEATURE:
<223> OTHER INFORMATION: sequence of adapter ligated with DNA fragment

<400> SEQUENCE: 19
taaatcggta gctccgcccc tgaccattat attttattga agtattattg ttgatcattg    60
atatccatta tattcatttg ctttagatta tcatatctt                          99

<210> SEQ ID NO 20
<211> LENGTH: 99
<212> TYPE: DNA
<213> ORGANISM: artificial
<220> FEATURE:
<223> OTHER INFORMATION: sequence of adapter ligated with DNA fragment

```
<400> SEQUENCE: 20
taaatcggta gctccgcccc tgaccattat attttattga agtattattg ttgatcattg      60
atatccatta tattcatttg ctttagatta tcatatctt                             99

<210> SEQ ID NO 21
<211> LENGTH: 96
<212> TYPE: DNA
<213> ORGANISM: artificial
<220> FEATURE:
<223> OTHER INFORMATION: sequence of adapter ligated with DNA fragment

<400> SEQUENCE: 21
taactgagta gctccgcccc tgaccattat attttattga agtattattg ttgatcattg      60
atatccatta tattcatttg ctttagatta tcatat                                96

<210> SEQ ID NO 22
<211> LENGTH: 97
<212> TYPE: DNA
<213> ORGANISM: artificial
<220> FEATURE:
<223> OTHER INFORMATION: sequence of adapter ligated with DNA fragment

<400> SEQUENCE: 22
taactgagta gctccgcccc tgaccattat attttattga agtattattg ttgatcattg      60
atatccatta tattcatttg ctttagatta tcatatt                               97

<210> SEQ ID NO 23
<211> LENGTH: 127
<212> TYPE: DNA
<213> ORGANISM: Petunia

<400> SEQUENCE: 23
ggctactgga gctgacaagc cagtgggaaa gcccaggacc ttagggatca agaaggcact      60
agtgttctat gctggaaaag cccctagagg aatcaagact aactggataa tgcacgagta     120
tcgtctc                                                               127

<210> SEQ ID NO 24
<211> LENGTH: 109
<212> TYPE: DNA
<213> ORGANISM: artificial
<220> FEATURE:
<223> OTHER INFORMATION: sequence of adapter ligated with DNA fragment

<400> SEQUENCE: 24
taaacaggta gctccgcccc tgcccaggac cttagggatc aagaaggcac tagtgttcta      60
tgctggaaaa gcccctagag gaatcaagac taactggata atgcacgag                 109

<210> SEQ ID NO 25
<211> LENGTH: 109
<212> TYPE: DNA
<213> ORGANISM: Artificial Sequence
<220> FEATURE:
<223> OTHER INFORMATION: sequence of adapter ligated with DNA fragment

<400> SEQUENCE: 25
taaagtggta gctccgcccc tgcccaggac cttagggatc aagaaggcac tagtgttcta      60
tgctggaaaa gcccctagag gaatcaagac taactggata atgcacgag                 109

<210> SEQ ID NO 26
<211> LENGTH: 107
```

```
<212> TYPE: DNA
<213> ORGANISM: Artificial Sequence
<220> FEATURE:
<223> OTHER INFORMATION: sequence of adapter ligated with DNA fragment

<400> SEQUENCE: 26
taagactgta gctccgcccc tgcccaggac cttagggatc aagaaggcac tagtgttcta      60
tgctggaaaa gccccctagag gaatcaagac taactggata atgcacg                 107

<210> SEQ ID NO 27
<211> LENGTH: 107
<212> TYPE: DNA
<213> ORGANISM: Artificial Sequence
<220> FEATURE:
<223> OTHER INFORMATION: sequence of adapter ligated with DNA fragment

<400> SEQUENCE: 27
taagactgta gctccgcccc tgcccaggac cttagggatc aagaaggcac tagtgttcta      60
tgctggaaaa gccccctagag gaatcaagac taactggata atgcacg                 107

<210> SEQ ID NO 28
<211> LENGTH: 77
<212> TYPE: PRT
<213> ORGANISM: Arabidopsis

<400> SEQUENCE: 28
```

Met Val Lys Lys Ser Lys Gly Arg Gln Lys Ile Glu Met Val Lys Met
1               5                   10                  15

Lys Asn Glu Ser Asn Leu Gln Val Thr Phe Ser Lys Arg Arg Ser Gly
            20                  25                  30

Leu Phe Lys Lys Ala Ser Glu Leu Cys Thr Leu Cys Gly Ala Glu Val
        35                  40                  45

Ala Ile Val Val Phe Ser Pro Gly Arg Lys Val Phe Ser Phe Gly His
    50                  55                  60

Pro Asn Val Asp Ser Val Ile Asp Asp Arg Phe Ile Asn
65                  70                  75

```
<210> SEQ ID NO 29
<211> LENGTH: 27
<212> TYPE: PRT
<213> ORGANISM: Arabidopsis

<400> SEQUENCE: 29
```

Cys Thr Leu Cys Gly Ala Glu Val Ala Ile Leu Ala Phe Ala Pro Asn
1               5                   10                  15

Ser Asn Lys Val Tyr Ser Phe Gly His Pro Cys
            20                  25

```
<210> SEQ ID NO 30
<211> LENGTH: 27
<212> TYPE: PRT
<213> ORGANISM: Arabidopsis

<400> SEQUENCE: 30
```

Cys Thr Leu Cys Gly Ala Glu Val Ala Ile Leu Ala Phe Ala Pro Asn
1               5                   10                  15

Ser Asn Lys Val Tyr Ser Phe Gly His Pro Cys
            20                  25

```
<210> SEQ ID NO 31
<211> LENGTH: 27
<212> TYPE: PRT
```

<213> ORGANISM: Arabidopsis

<400> SEQUENCE: 31

Cys Thr Leu Cys Gly Ala Glu Val Ala Ile Leu Ala Phe Ala Pro Asn
1               5                   10                  15

Ser Asn Lys Val Tyr Ser Phe Gly His Pro Cys
            20                  25

<210> SEQ ID NO 32
<211> LENGTH: 27
<212> TYPE: PRT
<213> ORGANISM: Arabidopsis

<400> SEQUENCE: 32

Cys Thr Leu Cys Gly Ala Glu Val Ala Ile Leu Ala Phe Ala Pro Asn
1               5                   10                  15

Ser Asn Lys Val Tyr Ser Phe Gly His Pro Cys
            20                  25

<210> SEQ ID NO 33
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 33
taaactggta gctccgcccc tggagatggt gcatgcaaag cagcgtatga taaaaggag      60 ttcatgttga agcaaatcaa ga                                              82

<210> SEQ ID NO 34
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 34
taaactggta gctccgcccc tggagatggt gcatgcaaag cagcgtatga taaaaggag      60 ttcatgttga agcaaatcaa ga                                              82

<210> SEQ ID NO 35
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 35
taacatggta gctccgcccc tggagatggt gcatgcaaag cagcgtatga taaaaggag      60 ttcatgttga agcaaatcaa ga                                              82

<210> SEQ ID NO 36
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 36
taagacagta gctccgcccc tggagatggt gcatgcaaag cagcgtatga taaaaggag      60 ttcatgttga agcaaatcaa ga                                              82

```
<210> SEQ ID NO 37
<211> LENGTH: 77
<212> TYPE: DNA
<213> ORGANISM: Artificial Sequence
<220> FEATURE:
<223> OTHER INFORMATION: sequence of adapter ligated with DNA fragment

<400> SEQUENCE: 37
taacatggta gctccgcccc tgacttttg tttgttgcac taagaaaaat tgcttactca        60
ggactcatcg tccaatt                                                      77

<210> SEQ ID NO 38
<211> LENGTH: 77
<212> TYPE: DNA
<213> ORGANISM: Artificial Sequence
<220> FEATURE:
<223> OTHER INFORMATION: sequence of adapter ligated with DNA fragment

<400> SEQUENCE: 38
taacatggta gctccgcccc tgacttttg tttgttgcac taagaaaaat tgcttactca        60
ggactcatcg tccaatt                                                      77

<210> SEQ ID NO 39
<211> LENGTH: 77
<212> TYPE: DNA
<213> ORGANISM: Artificial Sequence
<220> FEATURE:
<223> OTHER INFORMATION: sequence of adapter ligated with DNA fragment

<400> SEQUENCE: 39
taactgtgta gctccgcccc tgacttttg tttgttgcac taagaaaaat tgcttactca        60
ggactcatcg tccaatt                                                      77

<210> SEQ ID NO 40
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 40
taaagctgta gctccgcccc tggcaaacaa tgagataaac aataataaat aaatgaaatc        60
agtaaagctt attgtatttg aa                                                82

<210> SEQ ID NO 41
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 41
taaagctgta gctccgcccc tggcaaacaa tgagataaac aataataaat aaatgaaatc        60
agtaaagctt attgtatttg aa                                                82

<210> SEQ ID NO 42
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 42
```

```
taaagctgta gctccgcccc tggcaaacaa tgagataaac aataataaat aaatgaaatc      60
agtaaagctt attgtatttg aa                                              82
```

<210> SEQ ID NO 43
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 43

```
taaatcggta gctccgcccc tggcaaacaa tgagataaac aataataaat aaatgaaatc      60
agtaaagctt attgtatttg aa                                              82
```

<210> SEQ ID NO 44
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 44

```
taaatcggta gctccgcccc tggcaaacaa tgagataaac aataataaat aaatgaaatc      60
agtaaagctt attgtatttg aa                                              82
```

<210> SEQ ID NO 45
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 45

```
taaatcggta gctccgcccc tggcaaacaa tgagataaac aataataaat aaatgaaatc      60
agtaaagctt attgtatttg aa                                              82
```

<210> SEQ ID NO 46
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 46

```
taactgtgta gctccgcccc tggcaaacaa tgagataaac aataataaat aaatgaaatc      60
agtaaagctt attgtatttg aa                                              82
```

<210> SEQ ID NO 47
<211> LENGTH: 82
<212> TYPE: DNA
<213> ORGANISM: Artificial Sequence
<220> FEATURE:
<223> OTHER INFORMATION: sequence of adapter ligated with DNA fragment

<400> SEQUENCE: 47

```
taactgtgta gctccgcccc tggcaaacaa tgagataaac aataataaat aaatgaaatc      60
agtaaagctt attgtatttg aa                                              82
```

METHOD FOR THE HIGH THROUGHPUT SCREENING OF TRANSPOSON TAGGING POPULATIONS AND MASSIVE PARALLEL SEQUENCE IDENTIFICATION OF INSERTION SITES

FIELD OF THE INVENTION

The present invention relates to the fields of molecular biology and genetics. The invention relates to improved strategies for identifying mutants for genes in populations, based on the use of high throughput sequencing technologies

BACKGROUND OF THE INVENTION

Transposon tagging populations are used in modern plant genomics research to identify genes affecting traits of agronomic or general importance by reverse genetics approaches.

They represent complementary tools for gene discovery, as transposon populations are commonly used to identify the gene responsible for an observed phenotype, the so-called forward genetics approach. This is distinguished in the art from the reverse genetics approach wherein, mutational events are identified in sequences (genes) of interest. The rate-limiting step for the methods is the screening work associated with identification of the individual carrying a mutation in the gene or sequence of interest. Below, the principles of transposon populations and the screening methods are described in more detail and more efficient screening methods are presented which increase the value of these tools for gene-discovery.

Transposons are mobile genetic elements occurring, naturally or engineered, at multiple copies in the genome. They are unstable as their position in the genome can change by excision and insertion at novel sites, usually at any given moment in the life cycle. Transposon populations are valuable for gene-discovery because they can disrupt gene function if they insert in gene sequences or their regulatory regions. The sequences of many transposons used in plant breeding are known, but once a plant with an interesting phenotype is observed, it is not known which gene is affected by transposon insertion. It is, in general, also not known if and if so, which, transposon is responsible for the phenotype. Depending on the organism and transposon, copy numbers of transposons in transposon populations range from several tens to hundreds of transposon per plant.

Current screening methods for analysis of transposon-induced phenotypic mutant sequences include linked-PCR based methods in order to obtain flanking sequences from sequence-specific transposon integration sites. A limitation of linker-PCR is that determination of flanking sequences requires band-excision from sequencing gels, which is time-consuming, difficult to automate and relatively low-throughput (not easily adaptable to thousands of bands).

Screening transposon populations would be improved if a simple method would be available to collect flanking sequences of all or at least part of the transposons, integrated in the genome. Here we seek to provide an efficient approach to analyse and use insertion events in preferred sequences.

DEFINITIONS

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference. Transposon: Transposons are sequences of DNA that can move around to different positions within the genome of a single cell, a process called Transposition. In the process, they can cause mutations and change the amount of DNA in the genome. Transposons are also called "jumping genes" or "mobile genetic elements". There are a variety of mobile genetic elements; they can be grouped based on their mechanism of transposition. Class I mobile genetic elements, or retrotransposons, move in the genome by being transcribed to RNA and then back to DNA by reverse transcriptase, while class II mobile genetic elements move directly from one position to another within the genome using a transposase to "cut and paste" them within the genome. Transposition can be replicative wherein one copy of the transposable element remains at the donor site and another is inserted at the target site; or transposition can occur conservatively wherein the transposable element is excised from one site and inserted at the other. The term includes, but is not limited to, transposable elements found in prokaryotes such as insertion sequences (IS), transposons (Tn), or bacteriophages such as Mu and D108. Eukaryotic transposable elements include, but are not limited to: Copia transposable elements as are found in *D. melanogaster*; TY elements such as those found in yeast; Ta1 and Tnt 1 transposable elements such as those found in *Arabidopsis*; IAP found in mice; Tam or Cin transposable elements such as those found in snapdragon; and AC, Spm, Bs, Cin, Dt, and Mutator transposable elements such as those found in maize. The term is also inclusive of synthetic transposable elements which can insert themselves either replicatively or conservatively within a host genome and whose transposition or excision from the genome can be controlled by human intervention. For example, a synthetic transposable element can be constructed which lacks a functional transposase (the enzyme that mediates transposition) but which is supplied in trans by operably linking the transposase gene to an inducible promoter. Transposon population: A population of individual from one organism (usually plants, but other organisms, such as *Drosophila* and mouse are also possible), each of which carrying a plurality of transposons in their genome and each of which transposons may affect one or more genes, resulting in different phenotypes. Typically transposon populations can be obtained selected from individuals or varieties that express instability in a phenotypic trait. Transposon populations may vary widely in size, and for certain purposes, partial populations can be used that contain 90, 80 70, 60, 50, 40 30 or even only 20% of the original population.

Tag: A short sequence that can be added to a primer or included in its sequence or otherwise used as label to provide a unique identifier. Such a sequence identifier can be a unique base sequence of varying but defined length uniquely used for identifying a specific nucleic acid sample. For instance 4 bp tags allow 4 (exp4)=256 different tags. Typical examples are ZIP sequences, known in the art (Iannone et al. Cytometry 39:131-140, 2000). Using such a tag, the origin of a PCR sample can be determined upon further processing. In the case of combining processed products originating from different nucleic acid samples, the different nucleic acid samples are generally identified using different tags. In the case of the present invention, the addition of a unique sequence tag serves to identify the co-ordinates of the individual plant in the pool of sequences amplification products. Multiple tags can be used.

Tagging: refers to the process of the addition of a tag or label to a nucleic acid in order to be able to distinguish it from a second or further nucleic acid. Tagging can be performed, for example, by the addition of a sequence identifier during amplification by using tagged primers or by any other means known in the art.

Restriction endonuclease: a restriction endonuclease or restriction enzyme is an enzyme that recognises a specific nucleotide sequence (target site) in a double-stranded DNA molecule, and will cleave both strands of the DNA molecule at every target site.

Restriction fragments: the DNA molecules produced by digestion with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adaptors: short double-stranded DNA molecules with a limited number of base pairs, e.g. about 10 to about 30 base pairs in length, which are designed such that they can be ligated to the ends of restriction fragments. Adaptors are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adaptor molecule is designed such that it is compatible with the end of a restriction fragment and can be ligated thereto; the other end of the adaptor can be designed so that it cannot be ligated, but this needs not be the case (double ligated adaptors).

Adaptor-ligated restriction fragments: restriction fragments that have been capped by adaptors.

Nucleic acid: a nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

Sequencing: The term sequencing refers to determining the order of nucleotides (base sequences) in a nucleic acid sample, e.g. DNA or RNA.

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below. Sometimes the terms "assembly" or "clustering" are used as synonyms.

High-throughput screening: High-throughput screening, often abbreviated as HTS, is a method for scientific experimentation especially relevant to the fields of biology and chemistry. Through a combination of modern robotics and other specialised laboratory hardware, it allows a researcher to effectively screen large amounts of samples simultaneously.

Primers: in general, the term primer refers to a DNA strand which can prime the synthesis of DNA. DNA polymerase cannot synthesise DNA de novo without primers: it can only extend an existing DNA strand in a reaction in which the complementary strand is used as a template to direct the order of nucleotides to be assembled. We will refer to the synthetic oligonucleotide molecules which are used in a polymerase chain reaction (PCR) as primers.

Primers with increased affinity: Primers containing modified nucleotides such as PNA or LNA, which increase their thermal stability, which allows for more specific amplification based on single nucleotide sequence differences. In order to achieve this, one or several modified nucleotides are often included, preferably at the 3' end of the primer.

DNA amplification: the term DNA amplification will be typically used to denote the in vitro synthesis of double-stranded DNA molecules using PCR. It is noted that other amplification methods exist and they may be used in the present invention without departing from the gist thereof.

Selective hybridisation: relates to hybridisation, under stringent hybridisation conditions, of a nucleic acid sequence to a specified nucleic acid target sequence to a detectably greater degree (e.g., preferably at least 2-fold over background) than its hybridisation to non-target nucleic acid sequences and to the substantial exclusion of non-target nucleic acids. The terms "stringent conditions" or "stringent hybridisation conditions" includes reference to conditions under which a probe will hybridise to its target sequence, to a detectably greater degree than other sequences (e.g., preferably at least 2-fold over background). Stringent conditions are sequence-dependent and will be different in different circumstances. By controlling the stringency of the hybridisation and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 100 nucleotides in length, preferably no more than 50, or 25 nucleotides in length. Typically, stringent conditions will be those in which the salt concentration is less than about 1.5 M Na ion, typically about 0.01 to 1.0 M Na ion concentration (or other salts) at a pH of about 7.0 to 8.3 and the temperature is typically at least about 30° C. for short probes (e.g., 10 to 50 nucleotides) and typically at least about 60° C. for long probes (e.g., greater than 50 nucleotides). Stringent conditions may also be achieved with the addition of destabilising agents such as formamide. Exemplary low stringency conditions include hybridisation with a buffer solution of 30 to 35% formamide, 1 M NaCl, 1% SDS (sodium dodecylsulphate) at 37° C., and a wash in 1* to 2*SSC (20*SSC=3.0 M NaCl/0.3 M trisodium citrate) at 50 to 55° C. Exemplary moderate stringency conditions include hybridisation in 40 to 45% formamide, 1 M NaCl, 1% SDS at 37° C., and a wash in 0.5* to 1*SSC at 55 to 60° C. Exemplary high stringency conditions include hybridisation in 50% formamide, 1 M NaCl, 1% SDS at 37° C., and a wash in 0.1*SSC at 60 to 65° C. Specificity is typically the function of post-hybridisation washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridisation solution, and L is the length of the hybrid in base pairs. The Tm is the temperature (under defined ionic strength and pH) at which 50% of a complementary target sequence hybridises to a perfectly matched probe. Tm is reduced by about 1° C. for each 1% of mismatching; thus, Tm, hybridisation and/or wash conditions can be adjusted to hybridise to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilise a hybridisation and/or wash at 1, 2, 3, or 4° C. lower than the thermal melting point (Tm); moderately stringent conditions can utilise a hybridisation and/or wash at 6, 7, 8, 9, or 10° C. lower than the thermal melting point (Tm); low stringency conditions can utilise a hybridisation and/or wash at 11, 12, 13, 14, 15, or 20° C. lower than the thermal melting point (Tm). Using the equation, hybridisation and wash compositions, and desired Tm, those of ordinary skill will understand that variations in the stringency of hybridisation and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridisation of nucleic acids is found in Tijssen, Laboratory Techniques in Biochemistry and Molecular Biology-Hybridisation with Nucleic Acid Probes, Part 1, Chapter 2 "Overview of principles of hybridisation and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

DESCRIPTION OF THE INVENTION

The present inventors have found that by using high throughput sequencing strategies, the above-mentioned goals can be achieved and transposon populations, or populations comprising members carrying phenotypes of interest caused by transposon insertions, can be efficiently screened for the presence of insertions into genes of interest.

DETAILED DESCRIPTION OF THE INVENTION

The invention relates to a method for the identification of an insertion associated with a gene or sequence of interest in a member of a transposon population, comprising the steps of:

(a) isolating, individually or in pools, genomic DNA of the transposon population;
(b) optionally, pooling the DNA obtained in step (a);
(c) restrict the DNA using one or more, preferably two or more, most preferably two, restriction endonucleases, preferably at least one of which is a frequent cutting restriction endonuclease that does not cut in the transposon and preferably at least one is a rare cutting restriction endonuclease that cuts in the transposon, ligate adaptors to the restriction fragments to thereby prepare adaptor-ligated restriction fragments;
(d) amplifying the adaptor-ligated restriction fragments with a pair of (optionally labelled) primers, whereby one of the primers comprises a section that is complementary (capable of hybridising) to part of a (known) transposon sequence and further contains a sequence primer binding site, wherein the other primer is at least complementary to the adaptor, wherein one or both primers contain a tag;
(e) optionally, pooling the amplification products of step (d) to create a library of amplification products;
(f) optionally, fragmenting the amplification products in the library;
(g) determining the nucleotide sequence of the fragments of (d), (e) or (f) using high throughput sequencing;
(h) optionally, trimming the sequence of the fragments in silico to thereby remove any adaptor and/or transposon related sequence information;
(i) identifying one or more fragments of step (g) or (h) that are capable of aligning with nucleotide sequences from a database, thereby correlating the nucleotide sequences from the database with the phenotype of interest;
(j) identifying the member(s) of the transposon population containing the fragment(s) of step (i);
(k) optionally, designing a probe or PCR primer pair based on the fragments of step (i) and using it to confirm transposon insertion in the gene of interest in the genome of the member identified in (j).

The isolation of DNA to provide for DNA samples of each member in the population is generally achieved using common methods in the art such as the collection of tissue from a member of the population, DNA extraction (for instance using the Q-Biogene fast DNA kit), quantification and normalisation to obtain equal amounts of DNA per sample. As an example, the present invention is illustrated based on a transposon population of 1000 plants. Typically, DNA is isolated of each member of the population expressing the phenotype of interest.

In accordance with the method of the present invention, individual organisms whose genomic DNA comprises at least one transposable element-tagged gene can be segregated by the presence or absence of a mutant phenotype of interest. Thus a method is provided that is suitable for the identification and isolation of a genetic sequence from an organism, wherein disruption of genomic DNA of said organism by a transposable element flanking said genetic sequence is associated, directly or indirectly, with a mutant phenotype The mutant phenotype of the organism is preferably one known or suspected of arising from disruption of a single gene by insertion of a transposable element or, at the least, such an insertion event cannot be ruled out. In practice this may mean that a group of organisms are segregated based on the presence (or absence) of the mutant phenotype. Those of skill in the art will understand that the pool of organisms to be segregated should be grown or cultured under similar conditions to avoid segregation of phenotypes arising from non-genetic contributions (e.g., environmental effects). The method of the present invention can be applied to any phenotype which can be distinguished and classified as either wild-type or mutant. Such phenotypes can be detectable by visual, biochemical, agronomic, or morphological means. Those of skill will recognise that the terms "wild-type" and "mutant" as used herein are arbitrary terms used to differentiate organisms according to the presence or absence of a particular phenotype. The organisms to which the present invention can be applied can be prokaryotic or eukaryotic. Eukaryotic organisms can be haploid or diploid when employed in the methods of the present invention. In diploid organisms exhibiting the wild-type phenotype may be from the F1 generation, but mutant phenotypes associated with transposon-tagged genes more commonly show up as recessive mutants, and hence more commonly appear in the F2 generation. Thus, in a preferred embodiment of the invention, the organisms will be from the F2 generation of a cross between a transposable element-donor individual and a recipient inbred individual having no active transposable elements. Preferably, the methods of the present invention will be applied to plants. In certain embodiments, the preferred plant is a monocot such as those of the family Gramineae, including such exemplary species as Zea mays. In certain embodiments of the invention, the organisms having transposable elements will be maize plants from the F2 generation of a cross between a Mu-donor individual containing the Mu-DR regulatory element (Chomet et al. (1991) Genetics 122:447457) and high copy number of Mu elements and a recipient inbred individual having no active Mu elements. The genomic DNA of the organisms will have at least one transposable element, and preferably a plurality of transposable elements such as at least 5, 10, 25, 50, or 100. Transposable elements within the genome can be of the same or differing types. Organisms comprising transposable elements can be experimentally derived according to methods available in the art. See, for example, Chomet (1994) in The Maize Handbook, ed. Freeling and Walbot (Springer-Verlag, New York), pp. 243-248. In a preferred embodiment, the transposable element is Mutator (Mu). Robertson (1978) Mutation Res. 51:21-28, Chandler and Hardeman (1992) Advances in Genetics 30:77-122). The terminal-inverted-repeat DNA (TIR) present in many transposable elements, including Mu, is well suited to the present invention. Insertion of a transposable element may occur within or near a transposable element-tagged gene's DNA sequence. The transposable element-tagged gene to be identified with the method of the present invention may have a transposable element inserted within the gene's coding sequence, such that transcription of the gene's normal functional product is disrupted, leading to a mutant phenotype. Alternatively, the tagged gene may have a transposable element inserted within an intron, such that RNA splicing is affected, which in turn may disrupt the functional gene product, thereby yielding a mutant phenotype. Further, the tagged gene can have a transposable element inserted within a gene control region such as a promoter or enhancer element such that gene expression is increased or decreased leading to a mutant phenotype. For each phenotype to which the method of the present invention is applied, at least one organism having a wild-type phenotype and at least one mutant are segregated. Optionally, at least 2, 4, 5, 10, 15, or 20 organisms are present in the segregated wild-type population and at least 2, 4, 5, 10, 15, or 20 are present in the segregated mutant population.

The pooling of the isolated DNA can for instance be achieved using a 3-dimensional pooling scheme (Vandenbussche et al, 2003, The Plant Cell, 15, 2680-2693). The pooling is achieved preferably using equal amounts of DNA. The 3D-pooling scheme may comprise 10×10×10, resulting in 30 pools (10+10+10) containing 10×10=100 different DNA samples per pool. Various other pooling strategies can be used with the present invention, examples thereof are multidimensional pooling (incl. 3-D pooling) or column-, row- or plate pooling. In certain embodiments, pooling can also be performed before DNA extraction in the sampling stage, reducing the number of DNA preparations to 30 samples instead of 1000. (step (a) of the method).

The pooling step typically serves to identify the plant containing an observed transposon insertion after one round of PCR screening. Pooling of the DNA further serves to normalise the DNAs prior to PCR amplification to provide for a more equal representation in the libraries for sequencing. The DNA in the pools is restricted using at least one restriction endonuclease. Depending on the case, i.e. size of genome or number of transposons, more endonucleases can be used. In certain embodiments, 2 or more endonucleases can be used. For most genomes 2 endonucleases are sufficient and this is hence most preferred. In certain embodiments, especially for large or complex genomes, more endonucleases can be used. Preferably the endonuclease provides for relative short restriction fragments in the order of 50-500 bp, but this is not essential. Typically, at least one frequent cutting endonuclease is preferred, i.e. endonucleases that have a 4 or 5 base pair recognition sequence. One such enzyme is MseI, but numerous others are commercially available and can be used. Also enzymes that cut outside their recognition sequence can be used (IIs type), or enzymes that provide blunt ended restriction fragments. A preferred combination uses one rare (6 and more base pair recognition sequence) and one frequent cutter.

After restriction of the pooled DNAs, or simultaneously therewith, adaptors are ligated to the restriction fragments to provide for adaptor-ligated restriction fragments. One or more different adaptors may be used, for instance two adaptors, one forward, one reverse adaptor. Alternatively one adaptor may be used for all fragments or sets of adaptors may be used that at the overhanging end of the adaptor contain permutations of nucleotides such as to provide for indexing linkers that may allow for a pre-selection step (Unrau et al., Gene, 1994, 145, 163-169). Alternatively, blunt ended adaptors can be used, in the case of blunt ended restriction fragments. Adaptor-ligation is well known in the art and is described inter alia in EP 534858. After adaptor ligation, the pools of adaptor-ligated restriction fragments may be (pre-) amplified with a set of primers that are complementary to the adaptors. This may serve to (further) normalise the amount of DNA from each plant in the pools, or to increase the total amount of DNA in the pools to allow for multiple analysis of the pools (i.e. splitting up samples) and to enhance the signal-to-noise ratio.

The adaptor-ligated restriction fragments are, after the optional pre-amplification, amplified in step (d) of the method of the invention with a pair of primers. One of the primers is complementary to at least part of the adaptor and may further be complementary to part of the remainder of the recognition sequence of the endonuclease and may further contain (randomly selected) selective nucleotides at its 3'-end, similar as is described in EP534858. The other primer in the set of primers is designed such that is capable of annealing to (part of) a border of a transposon sequence. Typically, the primer overlaps with the consensus sequence of the transposon, and preferably at the border thereof. Preferably the primers are capable of selectively hybridising under stringent hybridisation conditions to the transposable element or the adaptor, respectively. Alternatively, the primer may overlap (is complementary) with the transposon for at least 50, 60, 70, 80, 85, 90, 95%. With an average length of a primer of about 20 bp, this amounts to an overlap of about 10 to 19 bases. This may be a consensus sequence or an actually known sequence of a transposon or transposon family in an organism. Typical transposon sequences in plants are known, see for instance: De Keukeleire et al. Chromosome Research, 2004, 12(2): 117-123; Van den Broeck et al., The Plant Journal, 1998, 13(1), 121-129; Gerats et al, Plant Cell, 1990, 2, 1121-1128 describing the 284 bp dTph1 transposition system in petunia. These references show that consensus sequence are known for transposon families, in particular at the borders of the transposons. Given these consensus sequence, design of suitable primers can readily be achieved. For example, the Hat family (Hobo, Ac and Tam3 in plants and animals. The transposon elements are known as well as their sequence from the following articles: Atkinson P W, Warren W D, O'Brochta D A (1993) The hobo transposable element of *Drosophila* can be cross-mobilized in houseflies and excises like the Ac element of maize. *Proc Natl Acad Sci USA* 90: 9693-9697; Capy P, Vitalis R, Langin T, Higuet D, Bazin C (1996) Relationships between transposable elements based upon the integrase-transposase domains: is there a common ancestor? *J Mol Evol* 42: 359-368; Esposito T, Gianfrancesco F, Ciccodicola A et al. (1999) A novel pseudoautosomal human gene encodes a putative protein similar to Ac-like transposases. *Hum Mol Genet.* 8: 61-67; Grappin P, Audeon C, Chupeau M C, Grandbastien M A (1996) Molecular and functional characterization of Slide, an Ac-like autonomous transposable element from tobacco. *Mol Gen Genet* 252: 386-397; Handler A M, Gomez S P (1996) The hobo transposable element excises and has related elements in tephridit species. *Genetics* 143: 1339-1347; Hehl R, Nacken W K, Krause A, Saedler H, Sommer H (1991) Structural analysis of Tam3, a transposable element from *Antirrhinum majus*, reveals homologies to the Ac element from maize. *Plant Mol Biol* 16: 369-371; Huttley G A, McRae A F, Clegg M T (1995) Molecular evolution of the Ac/Ds transposable element family in pearl millet and other grasses. Genetics 139: 1411-1419; Kempken F, Windhofer F (2001) The hAT family: a versatile transposon group common to plants, fungi, animals, and man. *Chromosoma* 110:1-9. Warren W D, Atkinson P W, O'Brochta D A (1995) The Australian bushfly *Musca vetustissima* contains a sequence related to transposons of the hobo, Ac and Tam3 family. *Gene* 154: 133-134.

Preferably, the transposon directed primer is oriented and designed such that it faces outward of the targeted transposon. In certain embodiment to enhance the specificity, the one or both primers, preferably the transposon directed primer, may contain nucleotides with improved binding affinity.

A part or segment of the adaptor-ligated restriction fragment is amplified using a pair of tagged primers, one or both of which may be labelled. Preferably, for each pool of each dimension, a different primer is used. In the above illustration this means that 30 forward and a single reverse primers are preferred. One of the forward and reverse primer may be directed towards the adapter and the other of the reverse and forward primer may be directed to the targeted transposon.

Preferably each pair of primers (the adapter directed primer and the transposon directed primer) may further comprise, dependently, one or more of the following elements:
(i) a sequence primer binding site that can be used in the following sequencing step,
(ii) a tag that serves to correlate the primer (and the resulting amplification product) to the original member of the population, and
(iii) a bead binding sequence that allows binding to the bead that is used in the high throughput sequencing step.

In a typical embodiment the transposon directed primer can have the following structure, both in 3'-5' direction and in 5'-3' direction:
Sequence primer binding site—optional Tag—Transposon specific PCR primer sequence or
Bead binding site—optional Tag—Transposon specific PCR primer sequence.

In a typical embodiment the adapter directed primer can have the following structure, both in 3'-5' direction and in 5'-3' direction:
Sequence primer binding site—optional Tag—adaptor specific PCR primer sequence or
Bead binding site—optional Tag—adaptor specific PCR primer sequence.

In certain embodiments, both the transposon directed primer and the adapter directed primer can be provided with 1-10 randomly selected nucleotides at the 3'-end that, when used in amplification may provide for subsets. See FIG. 1. The length of the sequence primer binding site and the transposon specific PCR primer sequence are those that are conventional in common PCR use, i.e., independently, from about 10 to about 30 bp with a preference for from 15 to 25 bp. Preferably the part or segment of the adaptor ligated sequence that is amplified corresponds to a length that can be sequenced in one run using the high throughput sequencing technologies described below. In certain embodiments, the part or segment has a length of between about 50 bp to about 500 bp, preferably from about 75 bp to about 300 bp and more preferably between about 90 bp and about 250 bp. As stated above, this length may vary with the sequencing technology employed including those yet to be developed.

Amplification with this set of primers will provide amplified adaptor-ligated restriction fragments (amplicons) of the flanking sequences of the targeted transposon in multiplex. By using primers (forward and/or reverse) containing a tag sequence that is unique for each of the primers representing all pool dimensions, the specific pool origin of each tag sequence is known as the sequence primer anneals upstream of the tag and as a consequence, the tag sequence is present in each amplification product.

In certain embodiments, both forward and reverse primers are tagged. In other embodiments, only one of the forward or reverse primers is tagged. The choice between one or two tags depends on the circumstances and depends on the read length of the high throughput sequencing reaction and/or the necessity of independent validation. In the case of, e.g., 100 bp PCR products that are sequenced unidirectionally, only one tag is needed. In the case of a 200 bp PCR product and a 100 bp read-length, double tagging is useful in combination with bi-directional sequencing as it improves efficiency 2-fold. It further provides the possibility of independent validation in the same step. When a 100 bp PCR product is sequenced bi-directionally with two tagged primers, all traces, regardless of orientation, will provide information about the mutation. Hence both primers provide "address information" about which plant contains which mutation. The tag can be any number of nucleotides, but preferably contains 2, 3, 4 or 5 nucleotides. With 4 nucleotides permuted, 256 tags are possible, whereas 3 nucleotides permuted provide 64 different tags. In the illustration used, the tags preferably differ by >1 base, so preferred tags are 4 bp in length. Amplification using these primers results in a library of tagged amplification products.

In certain embodiments, a system of tags can be used wherein the amplification process includes the use of a (1) a long primer comprising (a) a 5'-constant section linked to (b) a degenerate tag section (NNNN), linked to (c) a transposon or adaptor specific section-3' and
(2) a short primer in subsequent amplifications that consists of (a) the 5'-constant section linked to (b) non-degenerate tag section-3' (i.e. a selection amongst NNNN). The long primer is preferably used in a short measure and the short primer is used in an excess. The non-degenerate tag section can be unique for each pooled sample, for example, ACTG for pooled sample 1, AATC for pooled sample 2, etc. The short primer anneals to a subset of the long primer. The constant section of the primer can be used as a sequence primer. The library preferably comprises equal, amounts of PCR products from all amplified pools. In the illustrative example, the library contains 1000 plants×100 bp=100 kb sequence to be determined for each transposon insertion site. In step (e) of the method, the amplification products may be pooled, preferably in equal or normalised amounts to thereby create a library of amplification products. Exemplary, the complexity of the library will be 1000 plants×250-500 bp=0.25-0.5 Mb sequence for each transposon insertion site.

The amplification products in the library may be randomly fragmented prior to sequencing of the fragments.

Fragmentation can be achieved by physical techniques, i.e. shearing, sonication or other random fragmentation methods. In step (g), at least part, but preferably the entire, nucleotide sequence of at least part of, but preferably of all the fragments of step (d) or (f) is determined. In certain embodiments, the fragmentation step of the amplified products is optional. For instance, when the read length of the sequencing technique and the PCR fragments length are about the same there is no need for fragmentation. Also in the case of larger PCR products, fragmentation of the amplified products may not be necessary if it is acceptable that only part of them are sequenced. For instance in case of 500 bp PCR product and read length of 100 (from each side) 300 bp remain unsequenced in case of no fragmentation prior to sequencing. The need for fragmentation decreases with increasing read length of sequencing technology.

The sequencing may in principle be conducted by any means known in the art, such as the dideoxy chain termination method (Sanger sequencing). It is however preferred and more advantageous that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) Proc. Natl. Acad. Sci. USA 101:5488-93, and technologies of Helios, Solexa, US Genomics, etcetera, which are herein incorporated by reference. It is most preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described currently allows sequencing of up to 40 million bases in a single run and is 100 times faster and cheaper than competing technology. This will increase with increasing read length per reaction and/or increasing numbers of parallel reactions. The sequencing technology roughly consists of 5 steps: 1) fragmentation of DNA and ligation of specific adaptor to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of/enrichment for beads containing amplified ssDNA molecules on their surface 4) deposition of DNA carrying beads in a PicoTiterPlate®; and 5) simultaneous sequencing in 100,000 wells by generation of a pyrophosphate light signal.

In a preferred embodiment, the sequencing comprises the steps of:
(1) annealing sequencing-adaptor-ligated fragments to beads, each bead annealing with a single fragment;
(2) emulsifying the beads in water-in-oil micro reactors, each water-in-oil micro reactor comprising a single bead;
(3) performing emulsion PCR to amplify adaptor-ligated fragments on the surface of beads
(4) selecting/enriching beads containing amplified adaptor-ligated fragments
(6) loading the beads in wells, each well comprising a single bead; and
(7) generating a pyrophosphate signal.

In the first step (1), the adaptors that are present in the adaptor ligated restriction fragments are annealed to the beads. As outlined herein before, the sequencing adaptor includes at least a "key" region for annealing to a bead, a sequencing primer region and a PCR primer region. In particular, the amplified adaptor-ligated restriction fragments now contain at one of the ends the following sequence 5'-Sequence primer binding site—Tag—Transposon specific PCR primer sequence-3', while at the other end a segment is present that may be as follows: 5'-Bead annealing sequence—Tag—Adaptor specific sequence—restriction site specific sequence (optional)—(randomly) selective sequence (optional)-3'. It may be clear that the Sequence primer binding site and the Bead annealing sequence may be interchanged. This Bead annealing sequence can now be used for annealing the fragments to the bead, the bead carrying a nucleotide sequence to that end.

Thus, adapted fragments are annealed to beads, each bead annealing with a single adapted fragment. To the pool of adapted fragments, beads are added in excess as to ensure annealing of one single adapted fragment per bead for the majority of the beads (Poisson distribution).

In a preferred embodiment, to increase the efficiency of the transposon screening further, it is beneficial to amplify the transposed-derived PCR product directionally onto the bead for sequencing. This can be accomplished to perform the transposon PCR with adaptor-tailed PCR primers of which one strand of the adaptor on the MseI (or other restriction enzyme) side is complementary to the oligonucleotide coupled to the sequence beads. Hence the sequencing reaction will be primed from the transposon side (because sequencing occurs towards the bead), resulting in sequences that originate from the transposon outwards.

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PicoTiter™ Plate allowing for simultaneous sequencing of a large amount of fragments.

After addition of enzyme-carrying beads, the sequence of the fragments is determined using pyrosequencing. In successive steps, the PicoTiter™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia at two websites: one having the Worldwide Web URL biotagebio.com and the other at Worldwide Web URL pyrosequencing.com, at the table marked "Technology". The technology is further applied in e.g. WO 03/004690, WO 03/054142, WO 2004/069849, WO 2004/070005, WO 2004/070007, and WO 2005/003375 (all in the name of 454 Life Sciences), which are herein incorporated by reference.

After sequencing, the sequences of the fragments that are directly obtained from the sequencing step may be trimmed, preferably in silico, to remove any bead annealing sequence, sequencing primer, adaptor or transposon related sequence information. This may result in a better alignment in the next step with known sequences from the database to identify any possible hits. By doing this in silico, the information provided by the tag may be preserved in a separate database field so as to later on connect the discovered mutated gene to the address in the DNA pools.

Typically, the alignment or clustering is performed on sequence data that have been trimmed for any added adaptors/primer and/or identifier sequences i.e. using only the sequence data from the fragments that originate from the nucleic acid sample.

Methods of alignment of sequences for comparison purposes are well known in the art. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) Computer Appl. in the Biosci. 8:155-65; and Pearson et al. (1994) Meth. Mol. Biol. 24:307-31, which are herein incorporated by reference Altschul et al. (1994) Nature Genet. 6:119-29 (herein incorporated by reference) present a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx. A description of how to determine sequence identity using this program is available at the Worldwide Web URL ncbi.nlm.nih.gov/BLAST/blast_help.html. The database preferably comprises EST sequences, genomic sequences of the species of interest and/or the non-redundant sequence database of GenBank or similar sequence databases.

High throughput sequencing methods can be used as described in Shendure et al. *Science*, Vol 309, Issue 5741, 1728-1732. Examples thereof are microelectrophoretic sequencing, Hybridization sequencing/sequencing by hybridization (SBH), cyclic-array sequencing on amplified molecules, cyclic-array sequencing on single molecules, Non-cyclical, single-molecule, real-time methods, such as, polymerase sequencing, exonuclease sequencing, nanopore sequencing.

For an optimal result, it is of interest that the fragments or the amplified products are sequenced with sufficient redundancy. Redundancy is what enables making the distinction between sequencing errors and genuine genome sequences. In certain embodiments, the redundancy of the sequencing is preferable at least 4, more preferably at least 5, but as can be seen from the illustration, redundancies of more than 6, preferably more than 8 or even more than 10 are considered advantageous, although not essential for the inventive concept.

In step (i) of the method, the fragments are identified that yield a hit in the database and that hence may be linked to a gene or a phenotype of interest. Based on this information, the tags can be used to identify the pool and/or the plant. Based on the hit in the database, a probe can be designed that allows for the identification of the gene of interest.

DESCRIPTION OF THE FIGURES

Figure 2:
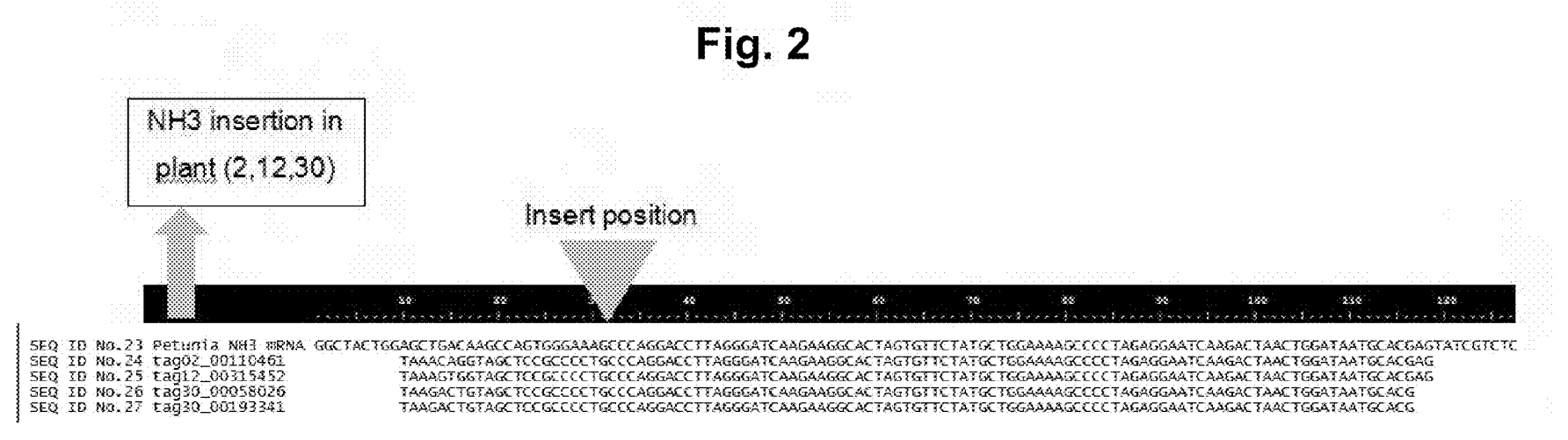

FIG. 2 describes the result of a blast search with a specific gene sequence, the Petunia transcription factor NAM-like 3 gene (no apical meristems like, gi|21105733| gb|AF509866.1), against the insertion flanking sequences database; an insertion hit is identified with the coordinates 2, 12, 30. This result demonstrates that insertions in specific homologous coding sequences can be traced. The 5 nucleotide sequences shown in FIG. 2 are, from top to bottom, SEQ ID NO: 23, 24, 25, 26, and 27.

FIG. 3 describes the result of a blast search with a specific but heterologous gene genic sequence, an Arabidopsis AGL62 MADS box gene, against the database; an insertion hit is identified in plant 9, 17, 29; this hit specifies a hitherto unknown potential MADS box gene in Petunia and its corresponding mutant. This result demonstrates that insertions in specific heterologous coding sequences are traced successfully. The 5 nucleotides sequences shown in FIG. 2 are, from top to bottom, SEQ ID NO: 28, 29, 30, 31 and 32.

FIG. 4 provides a sequence analysis wherein a subset of 230.000 of the available 318.000 sequences has been completely ordered according to three levels:
1) Sequence identity of the flanking sequences (ordering according to insertion site). All sequences identifying the same insertion are called one group.
2) Within groups, according to their differing 3D sequence tags.
3) According to copy number of sequences belonging to a group.

The following graphs have been extrapolated based on the analysis of 20% from 230.000 ordered sequences (of a total of 318.000 sequences). To facilitate interpretation of these graphs, 3 groups of sequences are shown in this figure, representing 3 independent transposon insertion sites. The first example identifies four sequences (SEQ ID NO:33, 34, 35 and 36); the second group of 3 sequences (SEQ ID NO: 37, 38 and 39; the third group of 8 sequences (SEQ ID NO: 40, 41, 42, 43, 44, 45, 46, 47, and 48), with the respective 3D tags spanning positions 5-8, followed by the Inverted Repeat sequence of the transposon, ending at position 22, followed by a stretch of genomic sequence. The coordinates 6-20-29 define this sequence as belonging to the plant at that particular coordinate of the population. Tag01 to tag10: X dimension, Tag11 to tag20: Y dimension, Tag21 to tag30: Z dimension.

Figure 1:
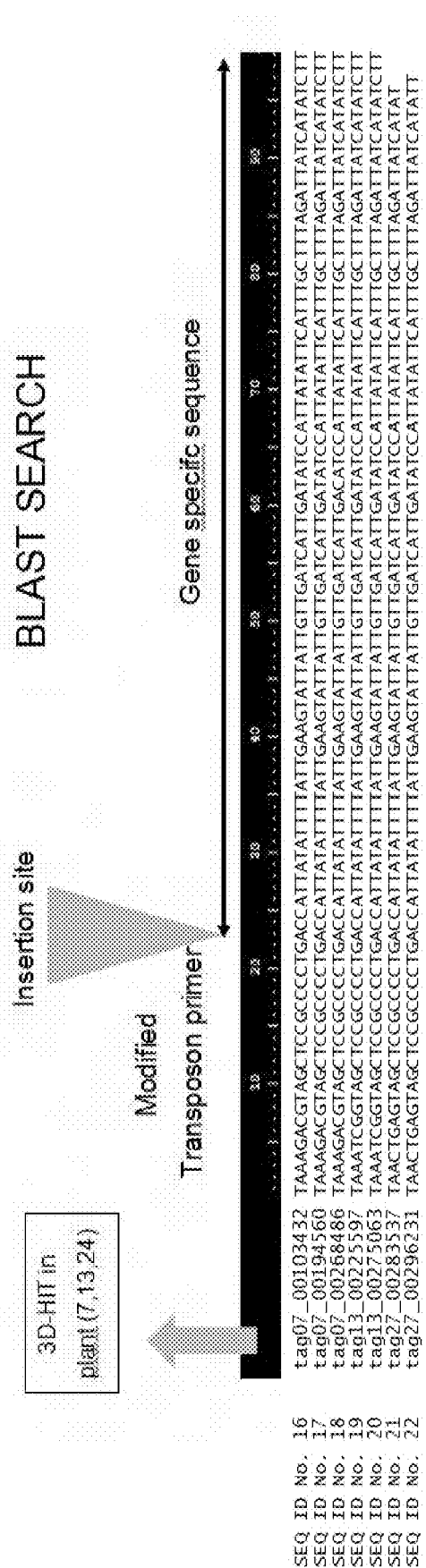
FIG. 1: In the distribution analysis of dtph1 transposon flanking sequences, the general built-up of a sequence tag, as consisting of (from right to left) a unique genomic sequence, the transposon (inverted repeat) sequence and the 3D tag is described. The population of 1000 plants is organized according to a 3D grid (10*10*10) in which each plant is identified according to a unique 3D coordinate (x, y, z) reflecting its position along the x, y and z axis. Dimensions X1 to X10 correspond to sequence tag numbers 1 to 10, similar for Y and Z. The tag codes in the figures are translated into tag # in the sequencename, e.g. AGAC corresponds to tag07. The picture shows the 3D hit in plant with pool coordinates (7. 13. 27). The 7 nucleotides sequences shown in FIG. 1 are, from top to bottom, SEQ ID NO:16, 17, 18, 19, 20, 21, and 22.
Figure 5:
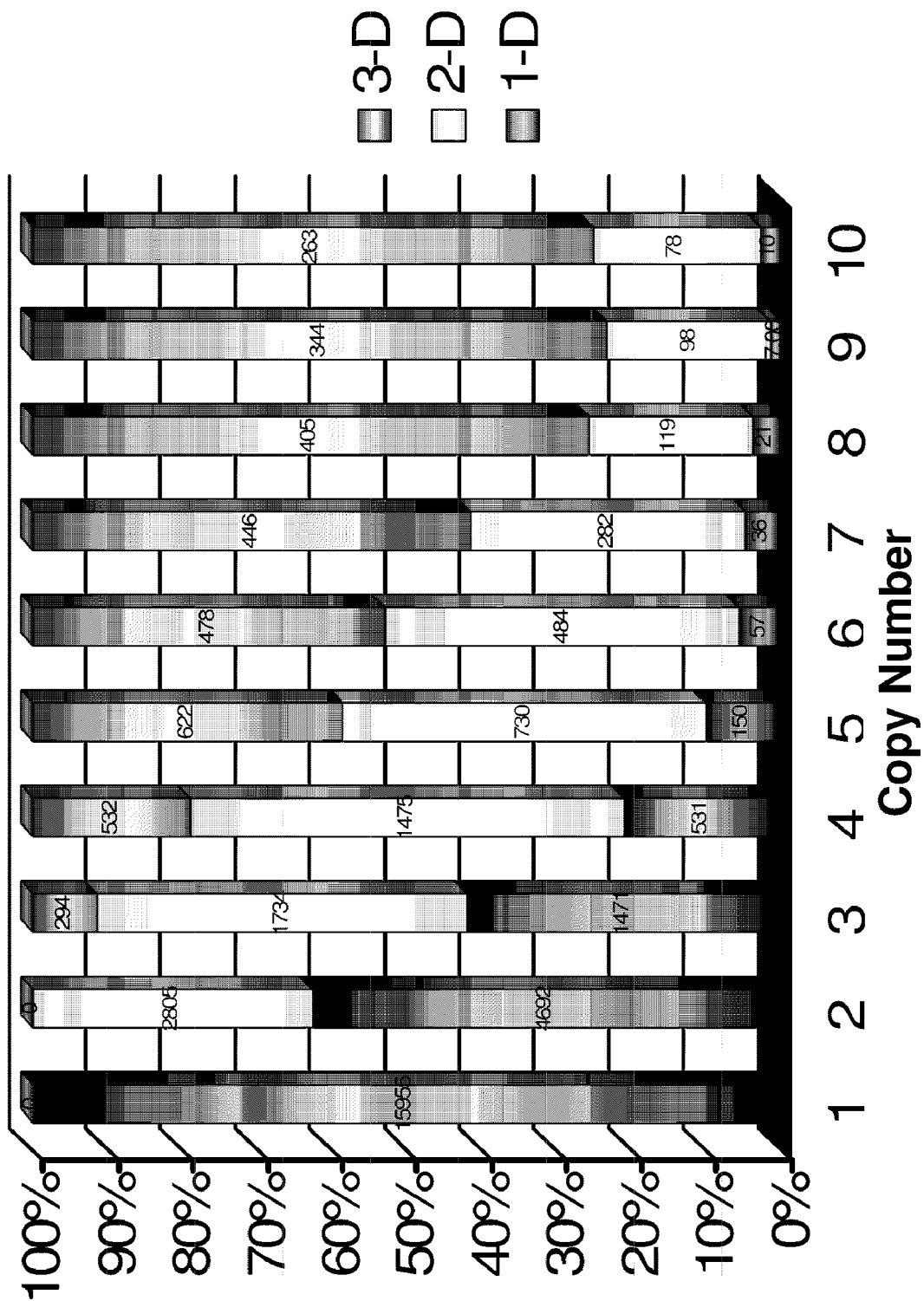

FIG. 5 provides a graphic display of the relative dimensional distribution versus copy number occurrence.

Figure 6:
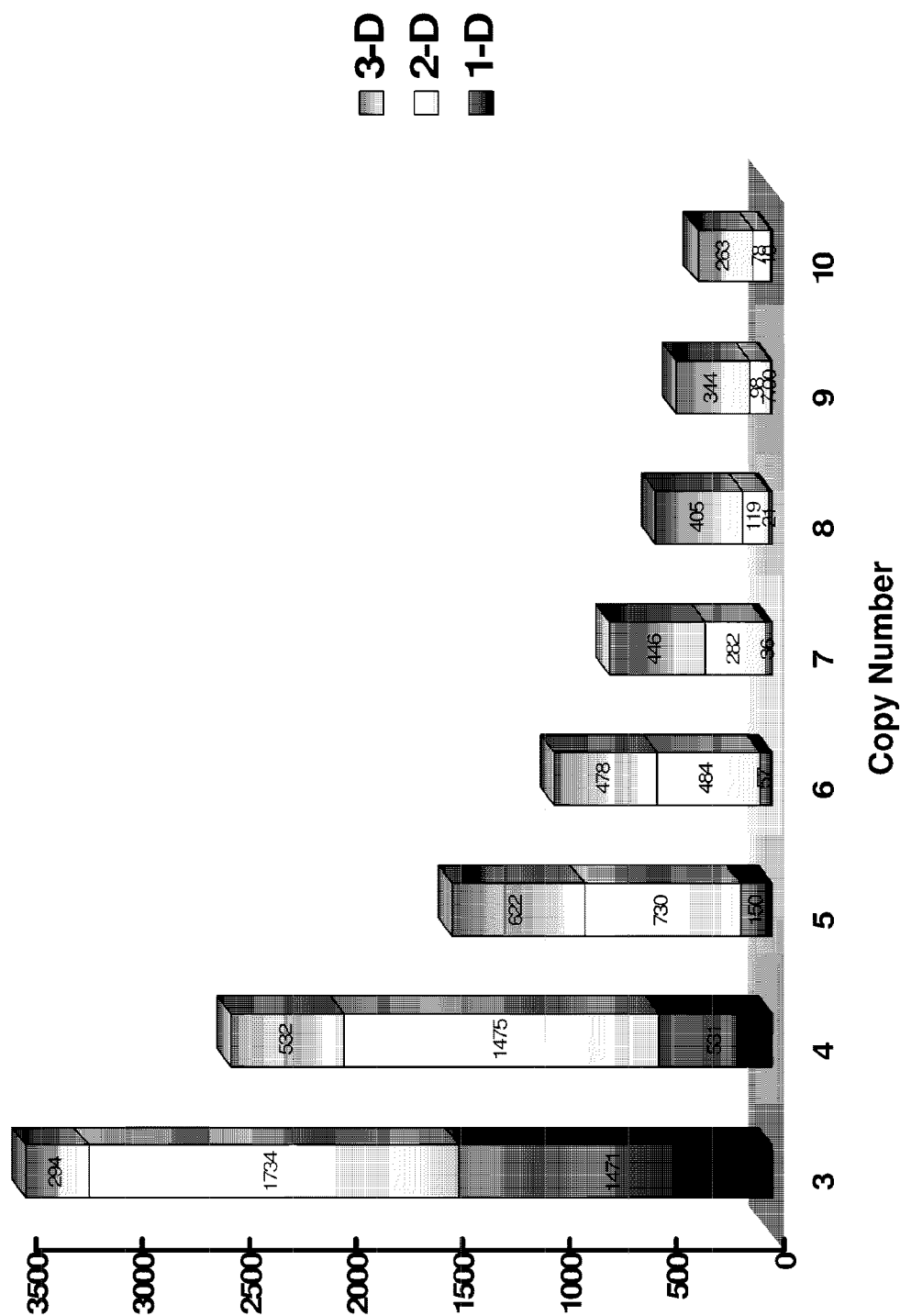

FIG. 6: Of the 3500 sequence tags that had three copies, 294 had 3 unique coordinates, meaning that these could trace back these sequences to their plant of origin. For the other copy classes those numbers were 532 for the four-copy class; 622 for the five-copy class; 478 for the six-copy class; and 1500 for the remaining classes. This implies that in total over 3000 sequence tags have been identified (out of 230.000 of the 318.000 available) that could be related back to their plant of origin.

Figure 7:
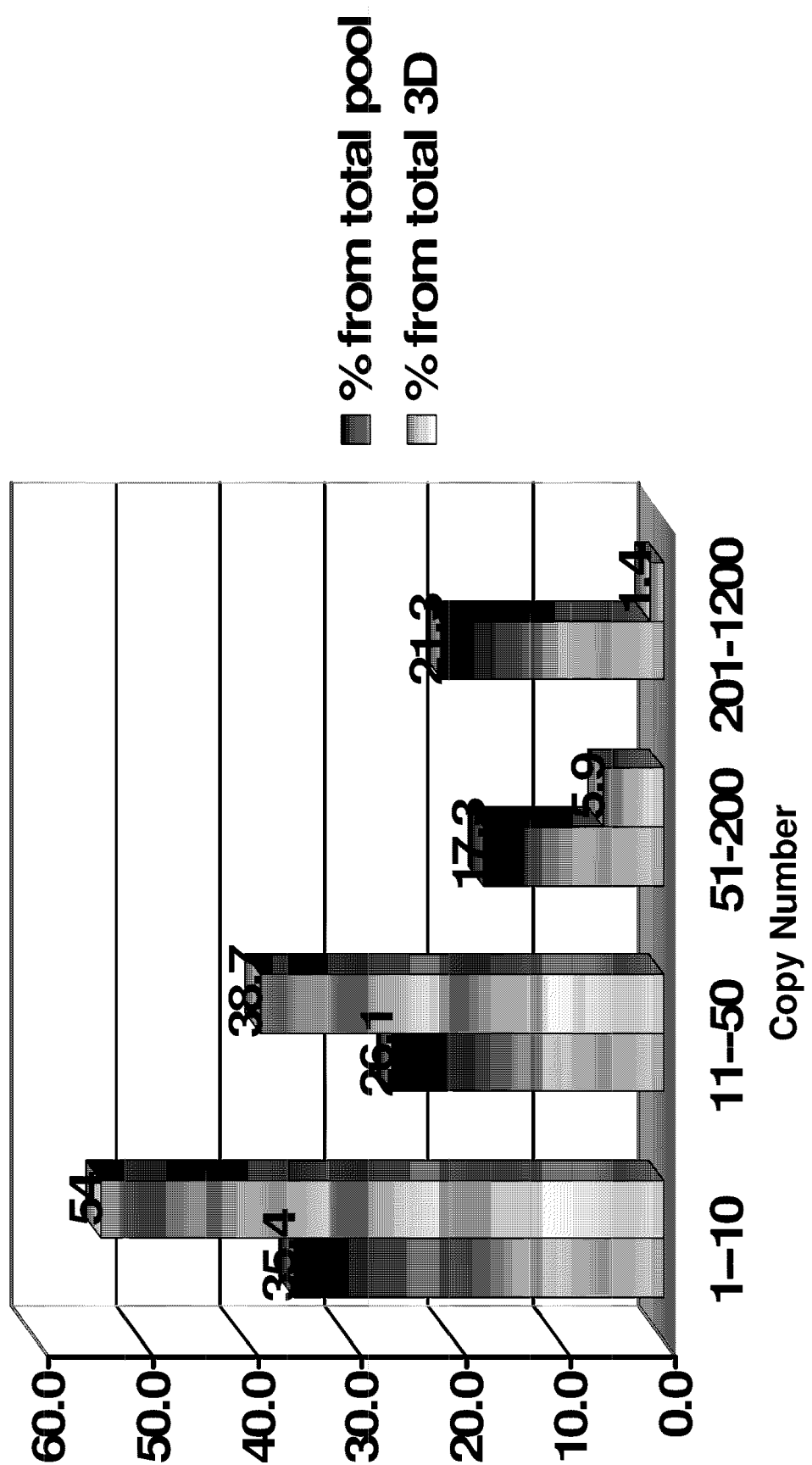
Figure 8:
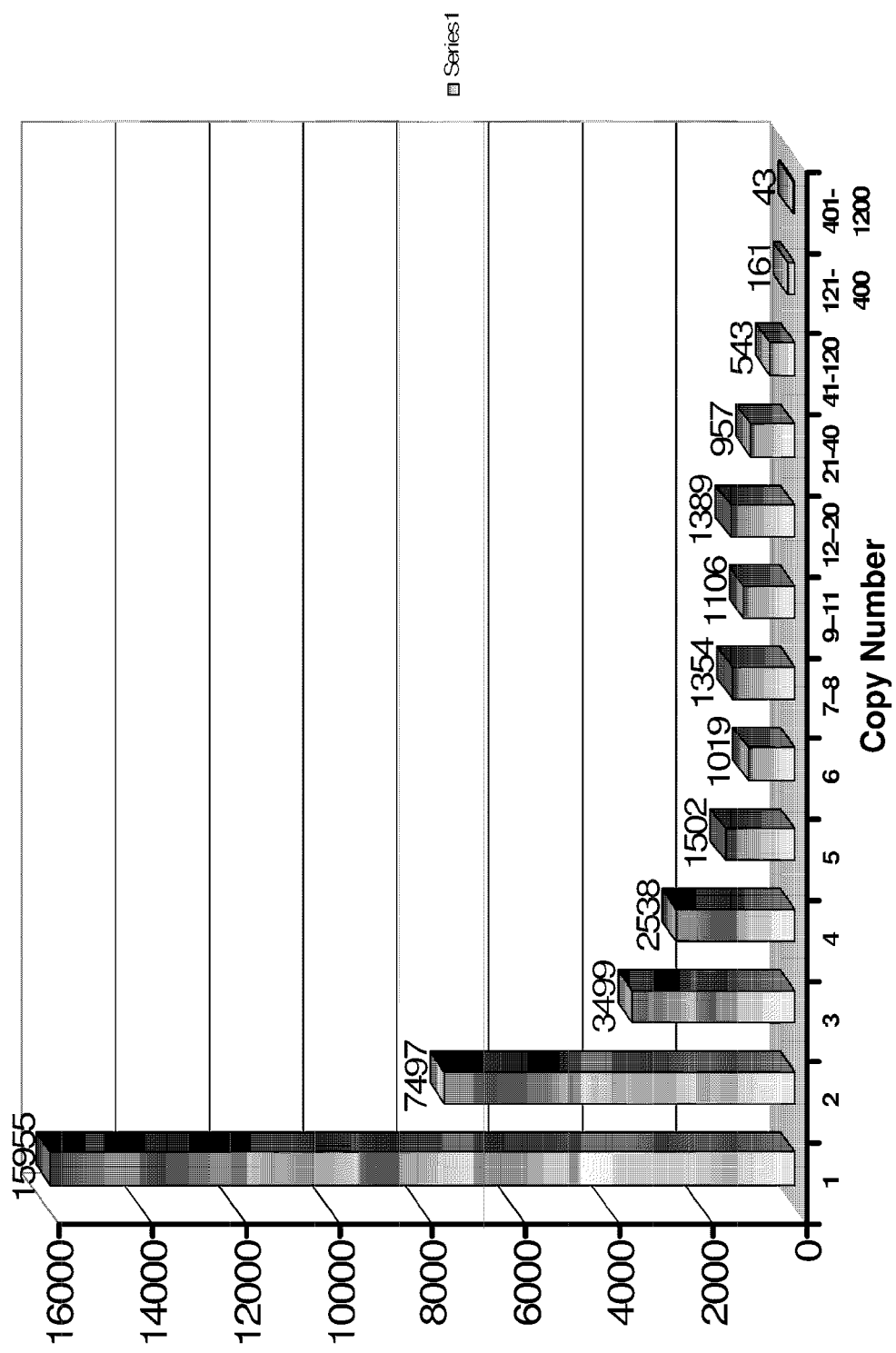

FIG. 7: 4 copy number classes and their relative contribution to total estimated 3D hit number and total number of sequences in 3D 454 transposon library FIG. 8: Number of # insertion sites (groups) versus copy number (full range) An analysis of the number of copies per sequence tag showed that amongst the 230.000 of the analysed subset, there were nearly 16.000 unique fragments; 7500 fragments had two copies; 3500 had three copies; 2500 had four copies; 1500 had five copies; 1000 had six copies; 1350 had 7 or 8 copies; 1100 had 9-11 copies; 1400 had 12-20 copies; 950 had 21-40 copies; while the remainder had the remaining copies.

Figure 9:
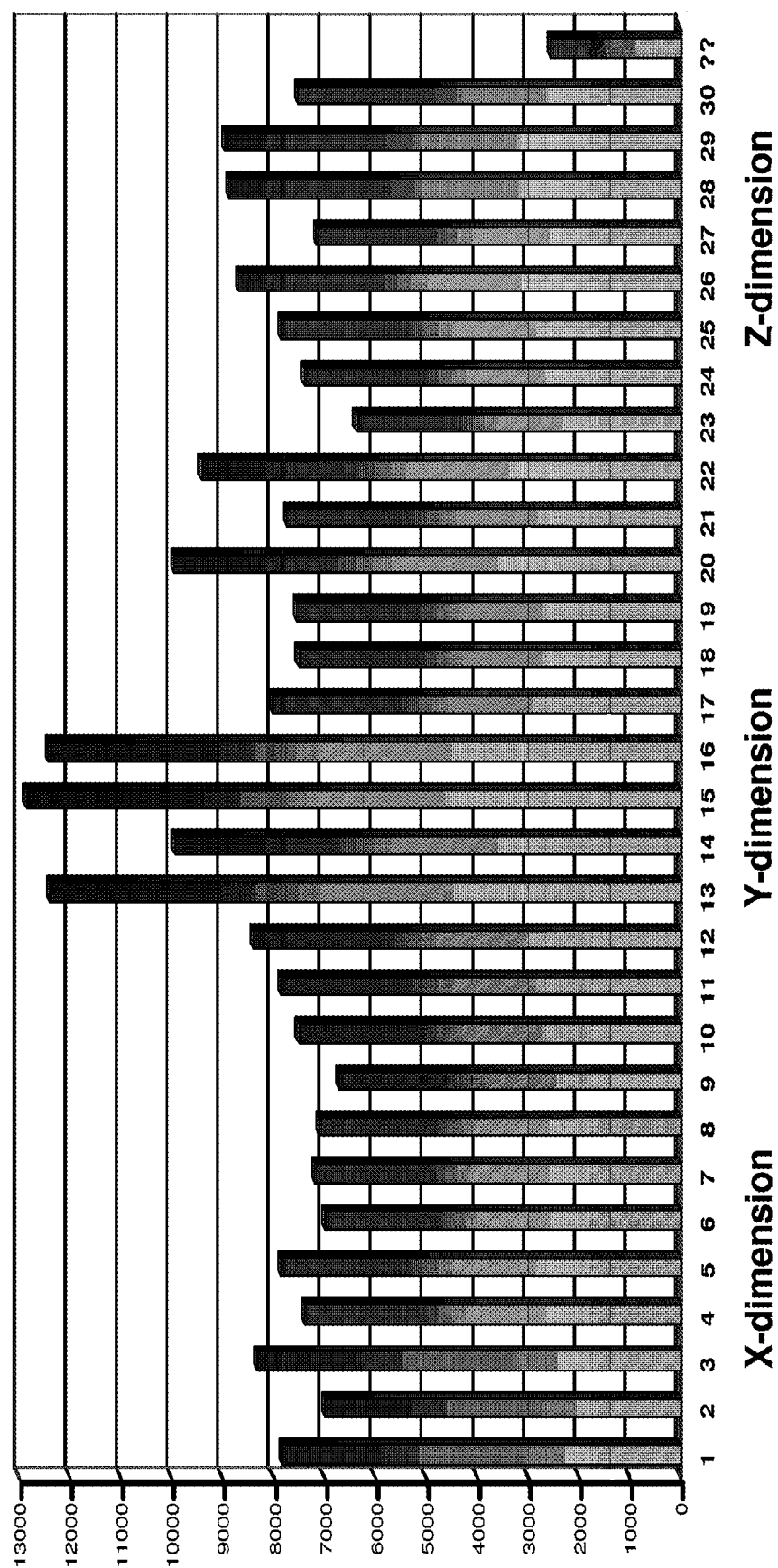

FIG. 9: provides a graphic display of some results. Subset of 253.394 sequences analyzed (total 318.000), Only 1% of the sequences did not contain a recognizable Tag (depicted as ??, right column) An analysis of 20% of the subset of 230.000 sequence tags indicated a good distribution of sequence tags over the different pooled samples of the population and ranged from over 6000 for coordinate 23 to nearly 30.000 for coordinate 15; the average being around 8500. Less then 1% of the fragments could not be assigned to a specific coordinate.

Figure 10:
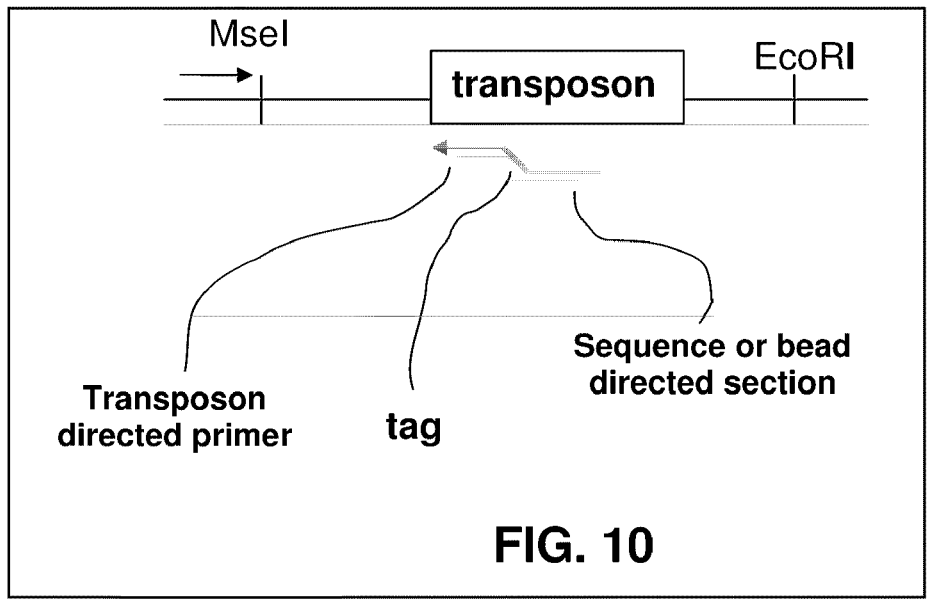

FIG. 10: Schematic illustration of a transposon targeted in a MseI-ECORI restriction fragment using an adaptor directed primer and a transposon directed primer carrying a tag and a bead annealing sequence.

Figure 11:

FIG. 11: Schematic representation of an amplified adaptor-ligated fragment annealed to a bead via a bead annealing sequence (B). The fragment contains tags (T1 and/or T2), the adaptor (AD), eventual remains of the restriction site (RE), the sequence of the fragment itself (SEQ), the transposon specific primer sequence (TR) and the sequence primer binding site (SPBS) used for the initiation of the sequencing step.

EXAMPLES

The present invention is illustrated with the following examples that provide illustration of the principle. Screening a transposon population is advanced by using novel high-throughput sequencing methods, such as that of 454 Life Sciences. With the current state-of-the-art, 454 Life Sciences technology produces approximately up to 40 Mb sequence in a single sequencing run. A limitation at present is that read lengths are approximately 100-200 bp/read. Assuming the screening of a population consisting of 3072 plants harbouring on average 200 transposons to identify transposon tagging of a particular gene, the approach is as follows:
1) Genomic DNA of 3072 plants of the transposon population is isolated;
2) A 3-dimensional pooling scheme of equal amounts of DNA per plant is set up (e.g. 15×15×14), resulting in 44 pools (15+15+14=44) containing 3072/14=219 or 3072/15=205 different DNA samples (Vandenbussche et al., 2003);

This pooling step serves to be able to identify the individual plant containing an insertion directly from the sequence data. Pooling of genomic DNAs further serves to normalise DNAs prior to PCR amplification to increase chances that all DNAs are represented equally in the sequence library;
3) adaptor ligated restriction fragment templates (AFLP templates, see EP534858, Vos et al NAR 1995, 23, 4407) are prepared from all 44 pooled DNAs using a single restriction enzyme that cuts the genome every 250-500 bp (e.g. using a 4- or 5 cutter; e.g. MseI);
4) unidirectional PCR amplification is carried out using a PCR primer located at the border of the transposon sequence and facing outwards and a non-selective adaptor primer, to amplify the flanking sequences of all transposon in multiplex. Per plant containing 200 transposons, this yields 200× approximately 250 bp=50 kb flanking sequence per border side, of which 20 kb will be sequenced in case of 100 bp read lengths. For 3072 plants this equals 153 Mb flanking sequence of which 61 Mb is sequencable in case of 100 bp sequence read lengths;
5) Equal amounts of PCR products from all 44 wells are pooled to create a pooled PCR product library;
6) The pooled PCR product library is sequenced using 454 Life Sciences sequencing-by-synthesis technology without further fractionation of PCR products. Output is approximately 200,000 100 bp sequences, representing 0.33×(20/61 Mb) coverage on average of all flanking sequences of 3072 plants. Hence at least 3 sequence runs are needed in order to target the vast majority of all flanking sequences of all 3072 plants;
7) resulting sequences are Blasted to identify hits with ESTs or genome sequences;
8) plants carrying transposon insertions in genes of interest are identified based on their tags and optionally probes or PCR primers are generated to confirm this.

Example 1

A population of 1000 Petunia W138 plants was sampled according to the 3-Dimensional strategy as described by Vandenbussche et al. (2003) and others, resulting in 30 pooled samples (X1-X10, Y1-Y10 and Z1-Z10), covering every individual of the whole population with three coordinates. This enabled tracing back the origin of any specific PCR product to the plant of origin within the population.

The DNA samples were then digested with an enzyme, cutting inside the transposon and an enzyme cutting at a specific but random position in the flanking genomic DNA.

Adapters were then ligated to allow subsequent PCR amplification of all digested fragments. A biotinylated adapter was ligated to the internal transposon site. The DNA samples were then purified and biotinylated fragments collected by adding Streptavidin beads and using a magnet. All flanking sequences from all transposon insertions present in every DNA pool were then amplified using an adapted transposon display protocol (VandenBroeck et al., 1998). For every pooled sample, X1-X10, Y1-Y10 and Z1-Z10, in the example, a different transposon primer was used, incorporating the corresponding pool coordinate as a 4 nucleotide code in its 5' end (3D-tag).

All PCR products were subsequently pooled in three superpools, one for each dimension, to enable normalization of the samples, according to procedures described in the art; with this step, fragments that are present in every individual and thus in every sample, are diminished in occurrence. This prevents over-representation of fragments in the samples-to-be-sequenced.

The obtained collections of single-stranded molecules were converted to double-stranded molecules by a single round of PCR amplification with a specific primer, harboring a MunI site.

The obtained products were digested with MunI/MseI in order to enable the subsequent ligation of adapter sequences that allow either further amplification or direct 454(G20) sequencing.

The three samples then were pooled in one superpool and subjected to the Roche GS20/454 sequencing procedure as described by the manufacturer.

A protocol was developed for the amplification of transposon flanking sequences by Transposon Display and subsequent high throughput sequencing from a population of 1000 plants.

Overview of the Procedure

An overview of the procedure is given below:
DNA preparation (1000 plants sampled in 3D fashion, resulting in 30 pooled DNA's)
MunI/MseI digest (ca 5 µg of Pooled DNA)
Bio-Mun & Mse adaptor ligation
Purification (PCR purification columns, to get rid of bio-Mun adaptors and very small fragments)
Beads extraction (enrichment of Mun/Mse fragments)
Transposon Display PCR amplifications:
Pre-amp with MunACAC & Mse+0 primers (enrichment of Transposon flanking sequences)
Selective PCR with Pooled specific IR**outw & Mse+0 primers (Amplification of Transposon Flanking Sequences)
Second pooling into "Block", "Row" and "Column" pools
Normalization
Conversion to double-stranded molecules
MunI/MseI digestion
454-Mun-B & 454-Mse-A adaptor ligation
PCR amplification with bio-AmpB & AmpA primers
Final pooling into one sample
454 sequencing
DNA Preparation
1000 plants sampled in 3D fashion, resulting in 30 DNA samples representing 100 plants each; procedure according to Vandenbussche et al., Plant Cell 15 (11): 2680-2693 (2003)
MunI/MseI digestion (ca. 5 µg)30 Samples
Ca. 5 µg DNA in 50 µl H$_2$O

| Add 20 µl mix: | 2 µl MunI (10 U/µl stock) |
| --- | --- |
| | 2 µl MseI (10 U/µl stock) |
| | 7 µl NEB 4 (10 × stock) |
| | 0.7 µl BSA (100 × stock) |
| | H$_2$O to 20 µl |

Incubate: 1.5 hrs. at 37° C.
Adapter Ligation:

| Add 30 µl mix | 8 µl MunI-bio-Adapter (5 pmol/µl stock) |
| --- | --- |
| | 8 µl MseI-Adapter (50 pmol/µl stock) |
| | 3 µl NEB 4 (10 × stock) |
| | 0.3 µl BSA (100 × stock) |
| | 3 µl ATP (10 mM stock) |
| | 3 µl T4 DNA ligase (5WeissU/µl stock) |
| | H$_2$O to 30 µl |

Incubate: 4 hrs. at 37° C.
Adapter Sequences:

```
Mun I (bio) adapter:
bio-5'-CTCGTAGACTGCGTACG-3'        SEQ ID NO: 1

3'-CTCGTAGACTGCGTACG-3'        SEQ ID NO: 2

Mse I adapter:
     5'-GACGATGAGTCCTGAG-3'         SEQ ID NO: 3

3'-TACTCAGGACTCAT-5'           SEQ ID NO: 4
```

Purification 30 Samples
Purify the DNA's, using the Qiagen PCR purification kit
Elute with 55 µl EB buffer (5 µl on 1.5% agarose gel)
Beads Extraction 30 Samples
Wash 25 µl streptavidine beads (ca. 0.1 mg MyOne beads, streptavidin C1) once in 200 µl STEX, and resuspend in 100 µl binding buffer.

| STEX: | Binding buffer: |
| --- | --- |
| 10 mM Tris•Cl (pH 8.0) | 10 mM Tris•Cl (pH 8.0) |
| 1 M NaCl | 2 M NaCl |
| 1 mM EDTA | 1 mM EDTA |
| 0.1% Triton X-100 | 0.1% Triton X-100 |

Add 100 µl diluted (&washed) Streptavidine beads to the 500 µl restriction/ligation mixture and incubate for 60 minutes on a rotator, at room temperature. Collect the beads, using the magnet and remove the supernatant. Wash the beads with 200 µl STEX and transfer to another tube. Wash the beads three times with 200 µl STEX and resuspend the beads finally in 50 µl T$_{01}$E, transfer to another tube (remove the STEX well).

T$_{01}$E:
10 mM Tris.Cl (pH8.0)
0.1 mM EDTA
Transposon Display PCR Amplifications: Pre-Amplification 30 Samples
Take 2 µl template DNA (mix the beads well, the DNA fragments are still connected) and add:

| 18 µl mix: | 0.6 µl Mun + ACAC primer (10 µM) |
| --- | --- |
| | 0.6 µl Mse + 0 primer (10 µM) |
| | 0.8 µl dNTP (5 mM) |
| | 2 µl 10 × PCR buffer |
| | 2 µl MgCl$_2$ (25 mM) |
| | 0.6 U Red Hot Taq DNA polymerase |
| | H$_2$O to 18 µl | and incubate them according to the following PCR profile (PE 9600):

| | 30" 94° C. | |
| --- | --- | --- |
| | 15" 94° C. | |
| Touchdown: | 30" 65° C. >> 56° C. ( ↑ t = −0.7° C./cycle) | \|13 |
| cycles | | |
| | 60" 72° C. | \| |
| | 15" 94° C. | \| |
| | 30" 56° C. | \| 22 cycles |
| | 60" 72° C. | \| |

Primer Sequences:

```
Mun I + ACAC:
5'-AGACTGTGTACGAATTGACAC-3'          SEQ ID NO: 5

Mse I + 0:
5'-GACGATGAGTCCTGAGTAA-3'            SEQ ID NO: 6
```

Analyse 5 μl on 1.5% agarose gel, and dilute the samples 10 times with H$_2$O and perform a selective PCR amplification:
Transposon Display PCR Amplifications:
Selective Amplification 30 Samples
Take 5 μl template DNA and add:

| 45 μl mix: | 1.5 μl IR$_{outw}$ primer (10 μM)* |
| --- | --- |
| | 1.5 μl Mse + 0 primer (10 μM) |
| | 2 μl dNTP (5 mM) |
| | 5 μl 10 × PCR buffer |
| | 5 μl MgCl$_2$ (25 mM) |
| | 1 U Red Hot Taq DNA polymerase |
| | H$_2$O to 45 μl |

And incubate them according to the following PCR profile (PE 9600).

| Touchdown: cycles | 30" 94° C. | |
| --- | --- | --- |
| | 15" 94° C. | |
| | 30" 65° C. >> 56° C. ($\hat{}$ t = −0.7° C./cycle) | \|13 |
| | 60" 72° C. | |
| | 15" 94° C. | |
| | 30" 56° C. | \|22 cycles |
| | 60" 72° C. | |

Primer Sequences:

```
                                     SEQ ID NO: 7
IR_outw:*   5'-CATATATTAANNNNGTAGCTCCGCCCCTG-3'
``` every pooled sample is amplified with a unique IR$_{outw}$ primer, specified by the NNNN positions; this allows to allocate obtained sequences to their co-ordinate of origin.

```
                                     SEQ ID NO: 8
Mse I + 0:   5'-GACGATGAGTCCTGAGTAA-3'
```

Second Pooling 30 Samples into 3 Samples
Pool the PCR products from the ten samples from each dimension to create 3 samples: column/row/block
Normalization.
In order to enhance the amount of unique fragments against a backdrop of fragments shared by many or all individuals, the second pooled samples are normalized, based on conventionally known procedures. The procedure involves a hybridisation and a purification step for obtaining single stranded molecules.
Hybridisation (about: 10 μg Each Sample) 3 Samples
Precipitate the DNA's of the Pooled samples and dissolve in 15-35 μl

| Add (relative volumes) to 15 μl formamid: | 4.5 μl TE |
| --- | --- |
| | 3 μl H$_2$O |

Heat to 80° C. under mineral oil for 3 minutes

| Add | 3 μl bufferA |
| --- | --- |
| | 4.5 μl H$_2$O |

Incubate the probe O/N at 30° C.
Buffer A:
0.1 M Tris.Cl (pH8.0)
1.2 M NaCl
50 mM EDTA
Purification by HAP Chromatography 3 Samples
Single stranded molecules are selected for by standard HAP chromatography as described by de Fatima Bonaldo et al., Genome Research, 6: 791-806 (1996) and subsequently converted to double-strand molecules.
Conversion to Double-Stranded Molecules 3 Samples
One PCR cycle with "Mse+0 with Mun site" primer add to 50 μl sample:

| 25 μl mix: | 5 μl MIBUS 796 (10 μM) |
| --- | --- |
| | 4 μl dNTP (5 mM) |
| | 7.5 μl 10 × PCR buffer |
| | 2.5 μl MgCl$_2$ (50 mM) |
| | 0.2 μl PlatinumTaq DNA polymerase |
| | H$_2$O to 25 μl |

Primer Sequence:

```
                                              SEQ ID NO: 9
MIBUS 796:  5'-CATATACAATTGGACGATGAGTCCTGAGTAA-3'
```

And incubate them according to the following profile (PE 9600):

| 2' | 94° C. |
| --- | --- |
| 1' | 56° C. |
| 10' | 72° C. |

MunI/Mse digest 3 Samples
Template DNA in 65 μH$_2$O

| Add 25 μl mix: | 2 μl MunI (10 U/μl stock) |
| --- | --- |
| | 2 μl MseI (10 U/μl stock) |
| | 9 μl NEB 4 (10 × stock) |
| | 0.9 μl BSA (100 × stock) |
| | H$_2$O to 25 μl |

Incubate: 1.5 hr. at 37° C.
454 Adapter Ligation

| Add | 4 μl MunI-bio-Adapter B (50 pmol/μl stock) |
| --- | --- |
| | 4 μl MseI-Adapter A (50 pmol/μl stock) |
| | 2 μl NEB 4 (10 × stock) |
| | 0.2 μl BSA (100 × stock) |
| | 3 μl ATP (10 mM stock) |
| | 3 μl T4 DNA ligase (5WeissU/μl stock) |
| | H$_2$O to 20 μl |

Incubate: 4 hrs. at 37° C.
Adapter Sequences:

```
Mun I adapter B:
MIBUS 803
                                           SEQ ID NO: 10
5'-CCTATCCCCTGTGTGCCTTGCCTATCCCCTGTTGCGTGTCTCAG-3'

MIBUS795
                                           SEQ ID NO: 11
3'-AGGGGACACACGGAACGGATAGGGGACAACGCACAGAGTCTTAA-5'

Mse I adapter A:
MIBUS 800
                                           SEQ ID NO: 12
5'-CCATCTCATCCCTGCGTGTCCCATCTGTTCCCTCCCTGTCTCAG-3'

MIBUS 801
                                           SEQ ID NO: 13
3'-GAGTAGGGACGCACAGGGTAGACAAGGGAGGGACAGAGTCAT-5'
```

PCR-Amplification for 454 Sequencing 3 Samples

```
   Amplification adaptor primer A & B:
                                        SEQ ID NO: 14
   MIBUS 803 bio-5'-CCTATCCCCTGTGTGCCTTG-3'

SEQ ID NO: 15
   MIBUS 802    5'-CCATCTCATCCCTGCGTGTC-3'
```

Final Pooling 3 Samples into 1 Sample

Pool the samples to create 1 superPool, ready for High throughput sequencing
454 Sequencing 1 Sample
pGEM-T Cloning for Insert Size Distribution Test1 Sample In order to test the efficiency of the normalisation procedure, we randomly isolated 22 fragments in order to determine their size distribution. Take 1 µl PCR mix (from the superpool sample for 454 sequencing)

| Add 4 µl mix: | 1 µl pGEM-T (4 times diluted) |
| --- | --- |
| | 2.5 µl 2 x rapid ligation buffer |
| | 0.25 µl Ligase |
| | H₂O to 4 µl |

Incubate: 3 hr. at 37° C.
Transform into *E. coli* (DH5α cells)
Plate 100 µl onto LB⁻ Amp plates
Incubate: o/n at 37° C.
Pick 22 colonies
Perform a PCR on boiled preps.
with the AmpA/AmpB primers
And run on a 2% agarose gel:
Results:

A database of 318.000 sequence tags of on average 102 basepairs was obtained. A subset of 230.000 sequences has been completely ordered according to three levels:

1) Sequence identity of the sequence, flanking the inverted repeat of the transposon (ending with CCGCCCCTG). All sequences identifying the same insertion are called one group.
2) Within each group, sequences are ordered according to the different 3D tags in their 5' sequence.
3) According to copy number of sequences belonging to a group.

The data have been extrapolated based on the analysis of 20% from 230.000 ordered sequences (of a total of 318.000 sequences). The analysis is described in the FIGS. 1-9.

TABLE

| | sequence | SEQ ID # |
| --- | --- | --- |
| Mun I (bio) adapter | bio-5'-CTCGTAGACTGCGTACG-3' | 1 |
| | 3'-CTGACGCATGCTTAA-5' | 2 |
| Mse I adapter | 5'-GACGATGAGTCCTGAG-3' | 3 |
| | 3'-TACTCAGGACTCAT-5' | 4 |
| Primer sequences | | |
| Mun I + ACAC: | 5'-AGACTGTGTACGAATTGACAC-3' | 5 |
| Mse I + 0: | 5'-GACGATGAGTCCTGAGTAA-3' | 6 |
| IR$_{outv}$:* | 5'-CATATATTAANNNNGTAGCTCCGCCCCTG-3' | 7 |
| Mse I + 0: | 5'-GACGATGAGTCCTGAGTAA-3' | 8 |
| MIBUS 796: | 5'-CATATACAATTGGACGATGAGTCCTGAGTAA-3' | 9 |
| Adapter sequences | | |
| Mun I adapter B: MIBUS 803 | 5'-CCTATCCCCTGTGTGCCTTGCCTATCCCCTGTTGCGTGTCTCAG-3' | 10 |
| MIBUS795 | 3'-AGGGGACACACGGAACGGATAGGGGACAACGCACAGAGTCTTAA-5' | 11 |
| Mse I adapter A:MTBUS 800 | 5'-CCATCTCATCCCTGCGTGTCCCATCTGTTCCCTCCCTGTCTCAG-3' | 12 |
| MIBUS 801 | 3'-GAGTAGGGACGCACAGGGTAGACAAGGGAGGGACAGAGTCAT-5' | 13 |
| Amplification adaptor primer A & B: | | |
| MIBUS 803 | bio-5'-CCTATCCCCTGTGTGCCTTG-3' | 14 |
| MIBUS 802 | 5'-CCATCTCATCCCTGCGTGTC-3' | 15 |

The invention claimed is:

1. A method for the identification of an insertion associated with a gene or sequence of interest in a member of a transposon population, comprising the steps of:
   (a) isolating, individually or in pools, genomic DNA of the transposon population;
   (b) optionally, pooling the DNA obtained in step (a);
   (c) restricting the DNA using one or more restriction endonucleases and ligating adaptors to the restriction fragments, thereby preparing adaptor-ligated restriction fragments;
   (d) amplifying the adaptor-ligated restriction fragments with a pair of primers, whereby one of the primers comprises a section that is complementary or capable of hybridizing to part of a transposon sequence and further comprises a sequencing primer binding site, wherein the other of the primers is at least complementary to the adaptor, wherein one or both primers comprise a tag;
   (e) optionally, pooling the amplification products of step (d) to create a library of amplification products;
   (f) optionally, fragmenting the amplification products in the library to create amplification library product fragments;
   (g) determining the nucleotide sequence of the fragments of (d), (e) or (f) using high throughput sequencing;
   (h) optionally, trimming the sequence of the fragments in silico to remove any adaptor and/or transposon related sequence information;
   (i) identifying one or more fragments of step (g) or (h) that are capable of aligning with nucleotide sequences from a database, thereby correlating the identified fragments with a gene or phenotype of interest represented in the database;
   (j) identifying members of the transposon population containing the fragment or fragments of step (i);
   (k) optionally, designing a probe or PCR primer pair based on the fragments of step (i) and using said probe or PCR primer to confirm transposon insertion in the gene of interest in the genome of the member or members identified in (j).

2. The method according to claim 1, wherein step (a) or step (b) uses a 3D-pooling strategy.

3. The method according to claim 1 wherein the database comprises EST sequences or genomic sequences of the species of interest.

4. The method according to claim 1, wherein the high throughput sequencing is based on Sanger sequencing.

5. The method according to claim 4, wherein the Sanger sequencing is performed by capillary electrophoresis.

6. The method according to claim 1, wherein the high throughput sequencing is sequencing-by-synthesis.

7. The method according to claim 6, wherein the sequencing-by-synthesis is pyrosequencing.

8. The method according to claim 1, wherein sequencing is performed on a solid support.

9. The method according to claim 8, wherein the solid support is a bead.

10. The method according to claim 9 wherein sequencing comprises the steps of:
    (1) annealing sequencing-adaptor-ligated fragments to beads, each bead annealing with a single fragment;
    (2) emulsifying the beads in water-in-oil microreactors, each water-in-oil microreactor comprising a single bead;
    (3) performing emulsion PCR to amplify adaptor-ligated fragments on the surface of beads;
    (4) selecting and/or enriching beads containing amplified adaptor-ligated fragments;
    (5) loading the beads into wells, one bead per well; and
    (6) generating a pyrophosphate signal.

11. The method according to claim 1, wherein at least one of the primers contains one or more nucleotides with improved binding affinity.

12. The method according to claim 1, wherein, in step (c), two or more restriction endonucleases are used.

13. The method according to claim 12, wherein, in step (c),
    (i) at least one the restriction endonucleases is a frequent cutting restriction endonuclease that does not cut in the transposon, and
    (ii) at least one of the restriction endonucleases is a rare cutting restriction endonuclease that cuts in the transposon.

14. The method according to claim 1, wherein in step (c) two restriction endonucleases are used.

15. The method according to claim 1, wherein, in step (d), the pair of primers is a pair of labeled primers.

* * * * *